US012616737B2

(12) United States Patent
Lundqvist

(10) Patent No.: US 12,616,737 B2
(45) Date of Patent: May 5, 2026

(54) LIQUID FORMULATIONS OF AMYLIN ANALOGUES

(71) Applicant: Zealand Pharma A/S, Søborg (DK)

(72) Inventor: Joakim Lundqvist, Søborg (DK)

(73) Assignee: Zealand Pharma A/S, Søborg (DK)

(*) Notice: Subject to any disclaimer, the term of this patent is extended or adjusted under 35 U.S.C. 154(b) by 0 days.

(21) Appl. No.: 18/707,536

(22) PCT Filed: May 30, 2023

(86) PCT No.: PCT/EP2023/064395
§ 371 (c)(1),
(2) Date: May 3, 2024

(87) PCT Pub. No.: WO2023/232781
PCT Pub. Date: Dec. 7, 2023

(65) Prior Publication Data

US 2024/0335513 A1 Oct. 10, 2024

(30) Foreign Application Priority Data

May 30, 2022 (EP) .................................... 22176247

(51) Int. Cl.
*A61K 38/22* (2006.01)
*A61K 47/18* (2017.01)

(52) U.S. Cl.
CPC .............. *A61K 38/22* (2013.01); *A61K 47/18* (2013.01)

(58) Field of Classification Search
CPC .......... A61K 38/22; A61K 47/18; A61K 9/08; A61K 47/02; A61K 47/183; A61K 9/0019; A61P 3/04; A61P 3/10
See application file for complete search history.

(56) References Cited

U.S. PATENT DOCUMENTS

| | | | |
|---|---|---|---|
| 5,424,394 | A | 6/1995 | Lehman de Gaeta et al. |
| 5,686,411 | A | 11/1997 | Gaeta et al. |
| 5,998,367 | A | 12/1999 | Gaeta et al. |
| 7,407,934 | B2 | 8/2008 | Kolterman et al. |
| 7,910,548 | B2 | 3/2011 | Duft et al. |
| 8,575,090 | B2 | 11/2013 | Schaeffer et al. |
| 8,575,091 | B1 | 11/2013 | Dahl et al. |
| 8,722,849 | B2 | 5/2014 | Schaeffer et al. |
| 8,741,836 | B2 | 6/2014 | Schaeffer et al. |
| 8,895,504 | B2 | 11/2014 | Schaffer et al. |
| 9,023,789 | B2 | 5/2015 | Dahl et al. |
| 10,071,140 | B2 | 9/2018 | Mathiesen et al. |
| 10,766,939 | B2 | 9/2020 | Just et al. |
| 11,129,877 | B2 | 9/2021 | Chan et al. |
| 11,382,956 | B2 | 7/2022 | Mathiesen et al. |
| 12,083,164 | B2 | 9/2024 | Mathiesen et al. |
| 2002/0187923 | A1 | 12/2002 | Gaeta et al. |
| 2008/0274952 | A1 | 11/2008 | Soares et al. |
| 2010/0221240 | A1 | 9/2010 | Kapurniotu et al. |
| 2013/0005646 | A1 | 1/2013 | Schaeffer et al. |
| 2013/0059770 | A1 | 3/2013 | Schaeffer et al. |
| 2014/0018286 | A1 | 1/2014 | Schaeffer et al. |
| 2014/0087995 | A1 | 3/2014 | Dahl et al. |
| 2016/0184401 | A1 | 6/2016 | Trambaioli Da Rocha E Lima et al. |
| 2016/0272693 | A1 | 9/2016 | Just et al. |
| 2018/0071366 | A1 | 3/2018 | Mathiesen et al. |

FOREIGN PATENT DOCUMENTS

| | | | |
|---|---|---|---|
| CL | 47901 | B1 | 9/2005 |
| CL | 2017002256 | A1 | 4/2018 |
| KR | 10-2017-0126504 | A | 11/2017 |
| TW | 201542588 | A | 11/2015 |
| TW | 201811818 | A | 4/2018 |
| WO | WO-91/07978 | A1 | 6/1991 |
| WO | WO-92/11862 | A1 | 7/1992 |
| WO | WO-9310146 | A1 | 5/1993 |
| WO | WO-9805351 | A1 | 2/1998 |
| WO | WO-98/08871 | A1 | 3/1998 |
| WO | WO-98/11125 | A1 | 3/1998 |
| WO | WO-98/26796 | A1 | 6/1998 |
| WO | WO-98/50059 | A1 | 11/1998 |
| WO | WO-98/55144 | A1 | 12/1998 |
| WO | WO-99/34764 | A2 | 7/1999 |
| WO | WO-9934822 | A1 | 7/1999 |
| WO | WO-2000/55119 | A1 | 9/2000 |
| WO | WO-2000/55184 | A1 | 9/2000 |
| WO | WO-2003/101395 | A2 | 12/2003 |
| WO | WO-2005/000222 | A2 | 1/2005 |
| WO | WO-2005/077072 | A2 | 8/2005 |
| WO | WO-2006042745 | A2 | 4/2006 |
| WO | WO-2006068910 | A1 | 6/2006 |
| WO | WO-2006/083254 | A1 | 8/2006 |
| WO | WO-2007/022123 | A2 | 2/2007 |

(Continued)

OTHER PUBLICATIONS

Gennaro A R (ed), Remington's Pharmaceutical Sciences, 1985, 17th edition, Mack Publishing Company, Easton, PA, U.S.A. (9 pages).
Groenning M et al., Study on the binding of ThioXavin T to -sheet-rich and non-sheet cavities, J. Struct. Biol., 2007, vol. 158, pp. 358-369 (12 pages).
Groenning, M., "Binding mode of Thioflavin T and other molecular probes in the context of amyloid fibrils-current status," J. Chem. Biol., 2010, vol. 3(1), pp. 1-18.
Jones, A J S, "Analysis of polypeptides and proteins," Adv. Drug Delivery Rev., (1993) vol. 10(1): 29-90 (62 pages).

(Continued)

*Primary Examiner* — Sudhakar Katakam
(74) *Attorney, Agent, or Firm* — Clark & Elbing LLP

(57) ABSTRACT

The present invention relates to formulations of amylin analogues, and their use, for example, in the treatment of obesity and metabolic disorders such as diabetes. In particular, the present invention relates to stable aqueous liquid formulations of amylin analogues.

19 Claims, No Drawings

Specification includes a Sequence Listing.

(56) References Cited

FOREIGN PATENT DOCUMENTS

| | | | | |
|---|---|---|---|---|
| WO | WO-2007/104789 A2 | 9/2007 | | |
| WO | WO-2008/101017 A2 | 8/2008 | | |
| WO | WO-2008/152403 A1 | 12/2008 | | |
| WO | WO-2009/034118 A1 | 3/2009 | | |
| WO | WO-2009/034119 A1 | 3/2009 | | |
| WO | WO-2010/046357 A1 | 4/2010 | | |
| WO | WO-2010/070251 A1 | 6/2010 | | |
| WO | WO-2010/070252 A1 | 6/2010 | | |
| WO | WO-2010/070253 A1 | 6/2010 | | |
| WO | WO-2010/070255 A1 | 6/2010 | | |
| WO | WO-2010/107874 A2 | 9/2010 | | |
| WO | WO-2011/006497 A1 | 1/2011 | | |
| WO | WO-2011/064282 A1 | 6/2011 | | |
| WO | WO-2011/160630 A2 | 12/2011 | | |
| WO | WO-2011/160633 A1 | 12/2011 | | |
| WO | WO-2012/168430 A2 | 12/2012 | | |
| WO | WO-2012/168431 A2 | 12/2012 | | |
| WO | WO-2012/168432 A1 | 12/2012 | | |
| WO | WO-2013/092703 A2 | 6/2013 | | |
| WO | WO-2013/156594 A1 | 10/2013 | | |
| WO | WO-2014/041195 A1 | 3/2014 | | |
| WO | WO-2014/197961 A1 | 12/2014 | | |
| WO | WO-2015/040182 A2 | 3/2015 | | |
| WO | WO-2015/050182 A1 | 4/2015 | | |
| WO | WO-2015/055801 A1 | 4/2015 | | |
| WO | WO-2015/055802 A2 | 4/2015 | | |
| WO | WO-2015/150564 A1 | 10/2015 | | |
| WO | WO-2015/168488 A2 | 11/2015 | | |
| WO | WO-2016/034604 A1 | 3/2016 | | |
| WO | WO-2016/100456 A2 | 6/2016 | | |
| WO | WO-2016/146739 A1 | 9/2016 | | |
| WO | WO-2018046719 A1 * | 3/2018 | ............ | A61K 38/22 |
| WO | WO-2018/144671 A1 | 8/2018 | | |
| WO | WO-2019122935 A1 | 6/2019 | | |
| WO | WO-2020051307 A1 | 3/2020 | | |
| WO | WO-2021185821 A1 | 9/2021 | | |

OTHER PUBLICATIONS

LeVine, H., III. "Thioflavine T interaction with synthetic Alzheimer's disease beta-amyloid peptides: detection of amyloid aggregation in solution," Protein Sci. vol 2(3):404-410 (1993) (7 pages).

Pearlman et al. Analysis of Protein Drugs,* *Peptide and Protein Drug Delivery*. Vincent H.L. Lee (ed), pp. 247-301 (1991) (57 pages).

Swarbrick J (ed) Encyclopaedia of Pharmaceutical Technology, 2007, Informa Healthcare (14 pages).

Yan L-M et al. "Design of a mimic of nonamyloidogenic and bioactive human islet amyload polypeptide (IAPP) as nanomolar affinity inhibitor of IAPP cytotoxic fibrillogenesis," Proc Natl Acad Sci. vol 103(7):2046-2051 (2006) (6 pages).

Yan L-M et al. "Selectively N-Methylated Soluble IAPP Mimics as Potent IAPP Receptor Agonists and Nanomolar Inhibitors of Cytotoxic Self-Assembly of Both IAPP and A-Beta-40," Angew. Chem. Int. Ed. 52(39):10378-10383 (2013) (6 pages).

Amino Acids Reference Chart, Sigma-Aldrich, 2014, downloaded from the internet Aug. 2014 (3 pages).

Baisley et al., "Amylin receptor signaling in the nucleus accumbens negatively modulates μ-opioid-driven feeding," Neuropsychopharmacology 39(13):3009-17 (2014) (9 pages).

Bogdanowich-Knipp et al., "Solution stability of linear vs. cyclic RGD peptides," J Pept Res. 53(5):530-41 (1999).

Chai et al., "Characterization of binding sites for amylin, calcitonin, and CGRP in primate kidney," Am J Physiol. 274(1 Pt 2):F51-62 (1998).

Database Geneseq [Online] Jun. 14, 2007, "Hybrid polypeptide amylin analog parent molecule Seq ID No 78.", XP002739549, retrieved from EBI accession No. GSP:AFC32081 Database accession No. AFC32081 (1 page).

Fortin et al., "Wildlife sequences of islet amyloid polypeptide (IAPP) identify critical species variants for fibrillization," Amyloid. 22(3):194-202 (2015) (9 pages). doi: 10.3109/13506129.2015.1070824.

Haffner et al., "Intensive lifestyle intervention or metformin on inflammation and coagulation in participants with impaired glucose tolerance," Diabetes. 54(5):1566-72 (2005) (14 pages).

He et al., "Synthesis and chemical stability of a disulfide bond in a model cyclic pentapeptide: Cyclo(1,4)-Cys-Gly-Phe-Cys-Gly-OH," J Pharm Sci. 95(10):2222-34 (2006).

International Preliminary Report on Patentability for International Application No. PCT/EP2016/055793, mailed Jun. 9, 2017 (37 pages).

International Search Report and Written Opinion for International Application No. PCT/EP2016/055793, mailed Jun. 24, 2016 (16 pages).

International Search Report and Written Opinion for International Application No. PCT/EP2017/072718, mailed Jan. 3, 2018 (13 pages).

Kajava et al., "A model for Ure2p prion filaments and other amyloids: the parallel superpleated beta-structure," Proc Natl Acad Sci U.S.A. 101(21):7885-90 (2004) (8 pages).

Knudsen et al., "Potent derivatives of glucagon-like peptide-1 with pharmacokinetic properties suitable for once daily administration," J Med Chem. 43(9):1664-9 (2000).

Koo et al., "Amide inequivalence in the fibrillar assembly of islet amyloid polypeptide," Protein Eng Des Sel. 21(3):147-54 (2008).

Li et al., "Suppression of polyglutamine toxicity by the yeast Sup35 prion domain in *Drosophila*," J Biol Chem. 282(52):37694-701 (2007) (9 pages).

Madsen et al., "Structure-activity and protraction relationship of long-acting glucagon-like peptide- 1 derivatives: importance of fatty acid length, polarity, and bulkiness," J Med Chem. 50(24):6126-32 (2007).

Moriarty et al., "Effects of sequential proline substitutions on amyloid formation by human amylin20-29," Biochemistry 38(6):1811-8 (1999).

Muthusamy et al., "Design and study of peptide-based inhibitors of amylin cytotoxicity," Bioorg Med Chem Lett. 20(4):1360-2 (2010).

Redalieu et al., "Pharmacokinetic Effects of Syringe Mixing Pramlintide, Isophane Insulin, and Soluble Insulin," Diabetology. 1399:A 356 (1997) (1 page).

Reidelberger et al., "Effects of amylin-related peptides on food intake, meal patterns, and gastric emptying in rats," Am J Physiol Regul Integr Comp Physiol. 282(5):R1395-404 (2002) (10 pages).

Rijkers et al., "Inhibition of amyloid fibril formation of human amylin by N-alkylated amino acid and alpha-hydroxy acid residue containing peptides," Chemistry 8(18):4285-91 (2002).

Tenidis et al., "Identification of a penta- and hexapeptide of islet amyloid polypeptide (IAPP) with amyloidogenic and cytotoxic properties," J Mol Biol. 295(4):1055-71 (2000).

Trivedi et al., "The role of thiols and disulfides on protein stability," Curr Protein Pept Sci. 10(6):614-25 (2009).

Tsai et al., "Energy landscape of amyloidogenic peptide oligomerization by parallel-tempering molecular dynamics simulation: significant role of Asn ladder," Proc Natl Acad Sci U.S.A. 102(23):8174-9 (2005) (9 pages).

Westermark et al., "Islet amyloid polypeptide: pinpointing amino acid residues linked to amyloid fibril formation," Proc Natl Acad Sci U.S.A. 87(13):5036-40 (1990).

Wineman-Fisher et al., "The removal of disulfide bonds in amylin oligomers leads to the conformational change of the 'native' amylin oligomers," Phys Chem Chem Phys. 18(18):12438-42 (2016).

International Search Report and Written Opinion for International Application No. PCT/EP2023/064395, mailed on Aug. 31, 2023 (14 pages).

Maikawa C L, Ultra-Fast Insulin-Pramlintide Co-Formulation for Improved Glucose Management in Diabetic Rats, Advanced Science, Sep. 9, 2021, vol. 8, No. 21 Article ID 2101575 (9 pages).

Mashkovsky M.D., "Medicines", Moscow, "Medicine", 1993, Part I, p. 8.

Kim, et al., "Effects of pH and buffer concentration on the thermal stability of etanercept using DSC and DLS," Biol Pharm Bull, 37(5): 808-816, (May 2014).

Frokjaer et al., Pharmaceutical Formulation Development of Peptides and Proteins, 3 pages, (2000).

(56) References Cited

OTHER PUBLICATIONS

Florence et al., Physicochemical principles of pharmacy, Third Edition, 3 pages (1998).
Chang et al. "Lyophilized Biologics in Lyophilized Biologics and Vaccines," Springer Science, 93-119 (2015).
Wang et al. "Technical Report No. 10 Parenteral Formulations of Proteins and Peptides: Stability and Stabilizers," Journal of Parenteral Science and Technology, Supplement , 42(S2): S22 (1998).
Zapadka et al. "Factors affecting the physical stability (aggregation) of peptide therapeutics," Interface Focus. (Oct. 20, 2017).

* cited by examiner

SEQUENCE LISTING

```
Sequence total quantity: 3
SEQ ID NO: 1            moltype = AA  length = 37
FEATURE                 Location/Qualifiers
DISULFID                2..7
                        note = A disulphide bridge is formed between residues at
                         positions 2 and 7
source                  1..37
                        mol_type = protein
                        organism = Homo sapiens
SEQUENCE: 1
KCNTATCATQ RLANFLVHSS NNFGAILSST NVGSNTY                          37

SEQ ID NO: 2            moltype = AA  length = 37
FEATURE                 Location/Qualifiers
DISULFID                2..7
                        note = A disulphide bridge is formed between residues at
                         positions 2 and 7
source                  1..37
                        mol_type = protein
                        organism = synthetic construct
SEQUENCE: 2
KCNTATCATQ RLANFLVHSS NNFGPILPPT NVGSNTY                          37

SEQ ID NO: 3            moltype = AA  length = 36
FEATURE                 Location/Qualifiers
REGION                  1..36
                        note = Synthetic amylin analogue
SITE                    1
                        note = X is isoGlu
SITE                    1
                        note = Linked to [19-carboxynonadecanoyl]
CROSSLNK                3..8
                        note = An amide bond is formed between the side chains at
                         positions 3 and 8
MOD_RES                 15
                        note = Aad
MOD_RES                 23
                        note = MeGly
MOD_RES                 25
                        note = MeIle
MOD_RES                 36
                        note = 4Hyp
source                  1..36
                        mol_type = protein
                        organism = synthetic construct
MOD_RES                 36
                        note = Amidation
SEQUENCE: 3
XRDGTATKAT ERLAXFLQRS SFGAILSSTE VGSNTX                           36
```

LIQUID FORMULATIONS OF AMYLIN ANALOGUES

SEQUENCE LISTING

The instant application contains a Sequence Listing which has been submitted electronically in XML format and is hereby incorporated by reference in its entirety. Said XML copy, created on May 3, 2024, is named "50412-151001_Sequence_Listing_5_3_24" and is 7,745 bytes in size.

FIELD OF THE INVENTION

The present invention relates to formulations of amylin analogues, and their use, for example, in the treatment of obesity and metabolic disorders such as diabetes. In particular, the present invention relates to stable aqueous liquid formulations of amylin analogues.

BACKGROUND OF THE INVENTION

Amylin is one of a family of peptide hormones that includes amylin, calcitonin, calcitonin gene-related peptide, adrenomedullin and intermedin (intermedin also being known as AFP-6), and has been implicated in various metabolic diseases and disorders. Human amylin was first isolated, purified and characterized as the major component of amyloid deposits in the islets of pancreases from type 2 diabetes patients.

Native human amylin is a 37-amino acid peptide having the formula (SEQ ID NO: 1)
H-KC()NTATC()ATQRLANFLVHSSNNFGAILSSTNVGSNTY-$NH_2$ wherein H- at the N-terminus designates a hydrogen atom, corresponding to the presence of a free amino group on the N-terminal amino acid residue [i.e. the lysine (K) residue at sequence position number 1 in the sequence shown above]; wherein —$NH_2$ at the C-terminus indicates that the C-terminal carboxyl group is in the amide form; and wherein the parentheses "( )" associated with the two cysteine (C, Cys) residues at sequence positions 2 and 7 indicate the presence of an intramolecular disulfide bridge between the two Cys residues in question.

Amylin may be beneficial in treating metabolic disorders such as diabetes and/or obesity. Amylin is believed to regulate gastric emptying, and to suppress glucagon secretion and food intake, thereby regulating the rate of glucose release to the circulation. Amylin appears to complement the actions of insulin. Compared to healthy adults, type 1 diabetes patients have no circulating amylin, and type 2 diabetes patients exhibit reduced postprandial amylin concentrations. In human trials an amylin analogue known as pramlintide, described in WO 93/10146 and having the sequence Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Pro-Ile-Leu-Pro-Pro-Thr-Asn-Val-Gly-Ser-Asn-Thr-Tyr (SEQ ID NO: 2), which also possesses a disulphide bridge between the Cys residues at positions 2 and 7, has been shown to reduce body weight or reduce weight gain.

An alternative amylin analogue incorporating N-methylated residues and having a reduced tendency to fibrillation, designated IAPP-GI, has been described by Yan et al. (PNAS, 103(7), 2046-2051, 2006; Angew. Chem. Int. Ed. 2013, 52, 10378-10383; WO2006/042745). IAPP-GI appears to have lower activity than native amylin, however.

WO 2018/046719 describes amylin analogues having, inter alia, a lactam bridge instead of a disulfide bridge, N-methylated residues, and a deletion corresponding to the residues Asn21 and Asn22 of native human amylin. Such analogues have considerably lower tendency towards fibrillation than native amylin, while also having higher potency than the analogues described by Yan et al. (supra). They are typically amenable to formulation at, or near to, physiological pH. However, there is a need to develop improved formulations for these analogues, especially to provide stable formulations capable of long-term storage without undue fibrillation or degradation of the active monomeric form of the peptide.

SUMMARY OF THE INVENTION

Broadly, the invention is based on studies described in the examples that led to surprising findings regarding aqueous formulations of the amylin analogue, that are particularly suitable for long term storage. In particular, it was found that a low buffer concentration and a particular pH range are unexpectedly significant for optimal stability.

The invention provides a stable aqueous liquid pharmaceutical formulation comprising an amylin analogue, which is:

(SEQ ID NO: 3)
[19CD]-isoGlu-RD( )GTATK( )ATERLA-Aad-FLQRSSF-
Gly(Me)-A-Ile(Me)-LSSTEVGSNT-Hyp-$NH_2$ or a pharmaceutically acceptable salt and/or derivative thereof;

wherein the formulation comprises:

(a) the amylin analogue at a concentration of from about 0.4 mg/ml to about 25 mg/ml; and (b) a buffer at a concentration of about 0.5 mM to about 25 mM;

wherein the formulation has a pH of about 5.8 to about 6.9.

The amylin analogue is present at a concentration of from about 0.4 mg/ml to about 25 mg/ml.

In some embodiments, the amylin analogue is present at a concentration of at least about 0.4 mg/ml, at least about 0.5 mg/ml, at least about 0.6 mg/ml, at least about 1.2 mg/ml, or at least about 2.5 mg/ml.

The amylin analogue may be present at up to about 25 mg/ml, up to about 20 mg/ml, up to about 15 mg/ml, or up to about 10 mg/ml.

The amylin analogue may be present at a concentration of about 3 mg/ml to about 12 mg/ml, e.g. about 3 mg/ml to about 7 mg/ml or about 8 mg/ml to about 12 mg/ml, e.g. about 5 mg/ml or about 10 mg/ml.

Any suitable buffer may be used, including a phosphate buffer, histidine buffer, TRIS buffer, acetate buffer, arginine buffer, citrate buffer, bicarbonate buffer, diethanolamine buffer, lysine buffer, TAPS buffer, succinate buffer, malate buffer, and α-ketoglutarate buffer. Particularly preferred buffers include phosphate buffer, histidine buffer, citrate buffer and TRIS buffer, especially phosphate buffer and histidine buffer.

Surprisingly, stability was found to be increased at relatively low buffer concentrations. Thus, the buffer is present at a concentration of about 0.5 mM to about 25 mM.

The buffer may be present at a concentration of about 0.5 mM to about 20 mM, e.g. about 0.5 mM to about 15 mM, e.g. about 1 mM to about 15 mM, e.g. about 1 mM to about 12 mM. For example, it may be present at a concentration of about 3 mM to about 7 mM or about 8 mM to about 12 mM, e.g. about 5 mM or about 10 mM, particularly (but not exclusively) when the buffer is phosphate, histidine or citrate.

For TRIS buffer, it may be preferred to be present at about 15 mM to about 25 mM, e.g. about 17 mM to about 23 mM, e.g. about 20 mM, since the buffering capacity of TRIS is lower than that of other buffers such as (e.g.) phosphate and histidine in the relevant pH range.

The pH of the formulation was also found to be significant for stability. The compounds described in WO 2018/046719 were believed to be stable at physiological pH (e.g. around pH 7.4) but it was surprisingly found that chemical stability was increased at lower pH values and physical stability was maintained. Thus, the formulation has a pH of about 5.8 to about 6.9, and may, for example, have a pH of about 6.2 to about 6.8, e.g. about 6.4 to about 6.6, e.g. about 6.5.

The stable aqueous liquid formulation may comprise a tonicity modifier. The tonicity modifier may be ionic or non-ionic. Suitable ionic tonicity modifiers include alkali metal salts (e.g. halides) and earth metal salts (e.g. halides), such as NaCl, NaBr, NaI, KCl, KBr, KI, LiCl, $CaCl_2$ and $Na_2SO_4$. Non-ionic tonicity modifiers include mannitol (e.g. D-mannitol), propylene glycol, sucrose, glycerol, sorbitol and trehalose.

In some embodiments, mannitol (e.g. D-mannitol), propylene glycol and NaCl may be preferred as tonicity modifiers, especially mannitol and propylene glycol.

The aqueous liquid formulation is typically stable for at least 6 months, e.g. at least 12 months, at least 18 months or at least 24 months, at 2-8° C. (e.g. at 5° C.). Preferably it is stable for at least 18 months, e.g. at least 24 months, at 2-8° C. (e.g. at 5° C.).

For example, the formulation may display substantially no changes indicative of reduced physical stability (e.g. as demonstrated by turbidity of the solution, or of aggregation, fibrillation or gelling of the amylin analogue) after it has been stored at 2-8° C. (e.g. at 5° C.) for at least 6 months, at least 12 months, at least 18 months, or at least 24 months. Preferably, the formulation displays substantially no such changes after it has been stored at 2-8° C. (e.g. at 5° C.) for at least 18 months, e.g. at least 24 months. It will be understood that accelerated conditions may also be employed as a proxy for assessing longer term physical stability as set out in more detail below.

Additionally, or alternatively, at least 80%, more preferably at least 85%, at least 90%, at least 95%, at least 96%, at least 97%, at least 98%, or at least 99% of the amylin analogue remains in intact monomeric form in the formulation after it has been stored at 2-8° C. (e.g. at 5° C.) for at least 6 months, at least 12 months, at least 18 months, or at least 24 months. Preferably, at least 90%, at least 95%, at least 96%, at least 97%, at least 98%, or at least 99% of the amylin analogue remains in intact monomeric form after it has been stored at 2-8° C. (e.g. at 5° C.) for at least 6 months, at least 12 months, at least 18 months, or at least 24 months. More preferably, at least 90%, at least 95%, at least 96%, at least 97%, at least 98%, or at least 99% of the amylin analogue remains in intact monomeric form in the formulation after it has been stored at 2-8° C. (e.g. at 5° C.) for at least 18 months, e.g. at least 24 months.

The formulation may further comprise a preservative, especially when it is provided in a multi-use format. Alternatively, and especially when provided in single-use format, the formulation may contain no or substantially no preservative.

The stable aqueous liquid formulation of the invention is formulated for parenteral administration, and in particular may be formulated for administration to a subject by injection, e.g. by subcutaneous injection.

In accordance with normal pharmaceutical practice, the formulations of the present invention are sterile and/or free (or substantially free, e.g. containing no more than about 100 ppm) of reducing agent.

An individual dose of a formulation of the invention may be provided in any suitable volume. For example, an individual dose may have a volume of 0.1 to 1.5 ml, for example 0.3 to 1.5 ml, for example 0.3 ml to 1 ml. Examples of specific individual dose volumes include 0.5 ml and 1 ml (e.g. 1.0 ml). Individual doses may be packaged separately for single use, e.g. in individual vials, cartridges or syringes, as described in more detail below.

By way of illustration, certain specific formulations may comprise or consist of the following:

Amylin analogue at a concentration of about 0.8 mg/ml, phosphate buffer at a concentration of about 5 mM, and mannitol at a concentration of about 250-260 mM; pH 6.5;

Amylin analogue at a concentration of about 1.2 mg/ml, phosphate buffer at a concentration of about 5 mM, and mannitol at a concentration of about 250-260 mM; pH 6.5;

Amylin analogue at a concentration of about 2.4 mg/ml, phosphate buffer at a concentration of about 5 mM, and mannitol at a concentration of about 250-260 mM; pH 6.5;

Amylin analogue at a concentration of about 4.8 mg/ml, phosphate buffer at a concentration of about 5 mM, and mannitol at a concentration of about 250-260 mM; pH 6.5;

Amylin analogue at a concentration of about 6.0 mg/ml, phosphate buffer at a concentration of about 5 mM, and mannitol at a concentration of about 250-260 mM; pH 6.5;

Amylin analogue at a concentration of about 9.0 mg/ml, phosphate buffer at a concentration of about 5 mM, and mannitol at a concentration of about 250-260 mM; pH 6.5;

Amylin analogue at a concentration of about 18 mg/ml, phosphate buffer at a concentration of about 5 mM, and mannitol at a concentration of about 250-260 mM; pH 6.5;

Amylin analogue at a concentration of about 0.8 mg/ml, phosphate buffer at a concentration of about 10 mM, and mannitol at a concentration of about 250-260 mM; pH 6.5;

Amylin analogue at a concentration of about 1.2 mg/ml, phosphate buffer at a concentration of about 10 mM, and mannitol at a concentration of about 250-260 mM; pH 6.5;

Amylin analogue at a concentration of about 2.4 mg/ml, phosphate buffer at a concentration of about 10 mM, and mannitol at a concentration of about 250-260 mM; pH 6.5;

Amylin analogue at a concentration of about 4.8 mg/ml, phosphate buffer at a concentration of about 10 mM, and mannitol at a concentration of about 250-260 mM; pH 6.5;

Amylin analogue at a concentration of about 6.0 mg/ml, phosphate buffer at a concentration of about 10 mM, and mannitol at a concentration of about 250-260 mM; pH 6.5;

Amylin analogue at a concentration of about 9.0 mg/ml, phosphate buffer at a concentration of about 10 mM, and mannitol at a concentration of about 250-260 mM; pH 6.5;

Amylin analogue at a concentration of about 18 mg/ml, phosphate buffer at a concentration of about 10 mM, and mannitol at a concentration of about 250-260 mM; pH 6.5.

Amylin analogue at a concentration of about 0.8 mg/ml, histidine buffer at a concentration of about 5 mM, and mannitol at a concentration of about 250-260 mM; pH 6.5;

Amylin analogue at a concentration of about 1.2 mg/ml, histidine buffer at a concentration of about 5 mM, and mannitol at a concentration of about 250-260 mM; pH 6.5;

Amylin analogue at a concentration of about 2.4 mg/ml, histidine buffer at a concentration of about 5 mM, and mannitol at a concentration of about 250-260 mM; pH 6.5;

Amylin analogue at a concentration of about 4.8 mg/ml, histidine buffer at a concentration of about 5 mM, and mannitol at a concentration of about 250-260 mM; pH 6.5;

Amylin analogue at a concentration of about 6.0 mg/ml, histidine buffer at a concentration of about 5 mM, and mannitol at a concentration of about 250-260 mM; pH 6.5;

Amylin analogue at a concentration of about 9.0 mg/ml, histidine buffer at a concentration of about 5 mM, and mannitol at a concentration of about 250-260 mM; pH 6.5;

Amylin analogue at a concentration of about 18 mg/ml, histidine buffer at a concentration of about 5 mM, and mannitol at a concentration of about 250-260 mM; pH 6.5;

Amylin analogue at a concentration of about 0.8 mg/ml, histidine buffer at a concentration of about 10 mM, and mannitol at a concentration of about 250-260 mM; pH 6.5;

Amylin analogue at a concentration of about 1.2 mg/ml, histidine buffer at a concentration of about 10 mM, and mannitol at a concentration of about 250-260 mM; pH 6.5;

Amylin analogue at a concentration of about 2.4 mg/ml, histidine buffer at a concentration of about 10 mM, and mannitol at a concentration of about 250-260 mM; pH 6.5;

Amylin analogue at a concentration of about 4.8 mg/ml, histidine buffer at a concentration of about 10 mM, and mannitol at a concentration of about 250-260 mM; pH 6.5;

Amylin analogue at a concentration of about 6.0 mg/ml, histidine buffer at a concentration of about 10 mM, and mannitol at a concentration of about 250-260 mM; pH 6.5;

Amylin analogue at a concentration of about 9.0 mg/ml, histidine buffer at a concentration of about 10 mM, and mannitol at a concentration of about 250-260 mM; pH 6.5;

Amylin analogue at a concentration of about 18 mg/ml, histidine buffer at a concentration of about 10 mM, and mannitol at a concentration of about 250-260 mM; pH 6.5.

Amylin analogue at a concentration of about 0.8 mg/ml, citrate buffer at a concentration of about 5 mM, and mannitol at a concentration of about 250-260 mM; pH 6.5;

Amylin analogue at a concentration of about 1.2 mg/ml, citrate buffer at a concentration of about 5 mM, and mannitol at a concentration of about 250-260 mM; pH 6.5;

Amylin analogue at a concentration of about 2.4 mg/ml, citrate buffer at a concentration of about 5 mM, and mannitol at a concentration of about 250-260 mM; pH 6.5;

Amylin analogue at a concentration of about 4.8 mg/ml, citrate buffer at a concentration of about 5 mM, and mannitol at a concentration of about 250-260 mM; pH 6.5;

Amylin analogue at a concentration of about 6.0 mg/ml, citrate buffer at a concentration of about 5 mM, and mannitol at a concentration of about 250-260 mM; pH 6.5;

Amylin analogue at a concentration of about 9.0 mg/ml, citrate buffer at a concentration of about 5 mM, and mannitol at a concentration of about 250-260 mM; pH 6.5;

Amylin analogue at a concentration of about 18 mg/ml, citrate buffer at a concentration of about 5 mM, and mannitol at a concentration of about 250-260 mM; pH 6.5;

Amylin analogue at a concentration of about 0.8 mg/ml, citrate buffer at a concentration of about 10 mM, and mannitol at a concentration of about 250-260 mM; pH 6.5;

Amylin analogue at a concentration of about 1.2 mg/ml, citrate buffer at a concentration of about 10 mM, and mannitol at a concentration of about 250-260 mM; pH 6.5;

Amylin analogue at a concentration of about 2.4 mg/ml, citrate buffer at a concentration of about 10 mM, and mannitol at a concentration of about 250-260 mM; pH 6.5;

Amylin analogue at a concentration of about 4.8 mg/ml, citrate buffer at a concentration of about 10 mM, and mannitol at a concentration of about 250-260 mM; pH 6.5;

Amylin analogue at a concentration of about 6.0 mg/ml, citrate buffer at a concentration of about 10 mM, and mannitol at a concentration of about 250-260 mM; pH 6.5;

Amylin analogue at a concentration of about 9.0 mg/ml, citrate buffer at a concentration of about 10 mM, and mannitol at a concentration of about 250-260 mM; pH 6.5;

Amylin analogue at a concentration of about 18 mg/ml, citrate buffer at a concentration of about 10 mM, and mannitol at a concentration of about 250-260 mM; pH 6.5.

These formulations may be particularly suitable for a dosing volume of 0.5 ml, although it will be understood that they may be used for other dosing volumes. Alternatively, the concentration of amylin analogue may be adjusted for a different dosing volume.

Further certain specific formulations may comprise or consist of the following:

Amylin analogue at a concentration of about 0.4 mg/ml, phosphate buffer at a concentration of about 5 mM, and mannitol at a concentration of about 250-260 mM; pH 6.5;

Amylin analogue at a concentration of about 0.6 mg/ml, phosphate buffer at a concentration of about 5 mM, and mannitol at a concentration of about 250-260 mM; pH 6.5;

Amylin analogue at a concentration of about 1.2 mg/ml, phosphate buffer at a concentration of about 5 mM, and mannitol at a concentration of about 250-260 mM; pH 6.5;

Amylin analogue at a concentration of about 2.4 mg/ml, phosphate buffer at a concentration of about 5 mM, and mannitol at a concentration of about 250-260 mM; pH 6.5;

Amylin analogue at a concentration of about 4.5 mg/ml, phosphate buffer at a concentration of about 5 mM, and mannitol at a concentration of about 250-260 mM; pH 6.5;

Amylin analogue at a concentration of about 9 mg/ml, phosphate buffer at a concentration of about 5 mM, and mannitol at a concentration of about 250-260 mM; pH 6.5;

Amylin analogue at a concentration of about 0.4 mg/ml, phosphate buffer at a concentration of about 10 mM, and mannitol at a concentration of about 250-260 mM; pH 6.5;

Amylin analogue at a concentration of about 0.6 mg/ml, phosphate buffer at a concentration of about 10 mM, and mannitol at a concentration of about 250-260 mM; pH 6.5;

Amylin analogue at a concentration of about 1.2 mg/ml, phosphate buffer at a concentration of about 10 mM, and mannitol at a concentration of about 250-260 mM; pH 6.5;

Amylin analogue at a concentration of about 2.4 mg/ml, phosphate buffer at a concentration of about 10 mM, and mannitol at a concentration of about 250-260 mM; pH 6.5;

Amylin analogue at a concentration of about 4.5 mg/ml, phosphate buffer at a concentration of about 10 mM, and mannitol at a concentration of about 250-260 mM; pH 6.5;

Amylin analogue at a concentration of about 9 mg/ml, phosphate buffer at a concentration of about 10 mM, and mannitol at a concentration of about 250-260 mM; pH 6.5.

Amylin analogue at a concentration of about 0.4 mg/ml, histidine buffer at a concentration of about 5 mM, and mannitol at a concentration of about 250-260 mM; pH 6.5;

Amylin analogue at a concentration of about 0.6 mg/ml, histidine buffer at a concentration of about 5 mM, and mannitol at a concentration of about 250-260 mM; pH 6.5;

Amylin analogue at a concentration of about 1.2 mg/ml, histidine buffer at a concentration of about 5 mM, and mannitol at a concentration of about 250-260 mM; pH 6.5;

Amylin analogue at a concentration of about 2.4 mg/ml, histidine buffer at a concentration of about 5 mM, and mannitol at a concentration of about 250-260 mM; pH 6.5;

Amylin analogue at a concentration of about 4.5 mg/ml, histidine buffer at a concentration of about 5 mM, and mannitol at a concentration of about 250-260 mM; pH 6.5;

Amylin analogue at a concentration of about 9 mg/ml, histidine buffer at a concentration of about 5 mM, and mannitol at a concentration of about 250-260 mM; pH 6.5;

Amylin analogue at a concentration of about 0.4 mg/ml, histidine buffer at a concentration of about 10 mM, and mannitol at a concentration of about 250-260 mM; pH 6.5;

Amylin analogue at a concentration of about 0.6 mg/ml, histidine buffer at a concentration of about 10 mM, and mannitol at a concentration of about 250-260 mM; pH 6.5;

Amylin analogue at a concentration of about 1.2 mg/ml, histidine buffer at a concentration of about 10 mM, and mannitol at a concentration of about 250-260 mM; pH 6.5;

Amylin analogue at a concentration of about 2.4 mg/ml, histidine buffer at a concentration of about 10 mM, and mannitol at a concentration of about 250-260 mM; pH 6.5;

Amylin analogue at a concentration of about 4.5 mg/ml, histidine buffer at a concentration of about 10 mM, and mannitol at a concentration of about 250-260 mM; pH 6.5;

Amylin analogue at a concentration of about 9 mg/ml, histidine buffer at a concentration of about 10 mM, and mannitol at a concentration of about 250-260 mM; pH 6.5.

Amylin analogue at a concentration of about 0.4 mg/ml, citrate buffer at a concentration of about 5 mM, and mannitol at a concentration of about 250-260 mM; pH 6.5;

Amylin analogue at a concentration of about 0.6 mg/ml, citrate buffer at a concentration of about 5 mM, and mannitol at a concentration of about 250-260 mM; pH 6.5;

Amylin analogue at a concentration of about 1.2 mg/ml, citrate buffer at a concentration of about 5 mM, and mannitol at a concentration of about 250-260 mM; pH 6.5;

Amylin analogue at a concentration of about 2.4 mg/ml, citrate buffer at a concentration of about 5 mM, and mannitol at a concentration of about 250-260 mM; pH 6.5;

Amylin analogue at a concentration of about 4.5 mg/ml, citrate buffer at a concentration of about 5 mM, and mannitol at a concentration of about 250-260 mM; pH 6.5;

Amylin analogue at a concentration of about 9 mg/ml, citrate buffer at a concentration of about 5 mM, and mannitol at a concentration of about 250-260 mM; pH 6.5;

Amylin analogue at a concentration of about 0.4 mg/ml, citrate buffer at a concentration of about 10 mM, and mannitol at a concentration of about 250-260 mM; pH 6.5;

Amylin analogue at a concentration of about 0.6 mg/ml, citrate buffer at a concentration of about 10 mM, and mannitol at a concentration of about 250-260 mM; pH 6.5;

Amylin analogue at a concentration of about 1.2 mg/ml, citrate buffer at a concentration of about 10 mM, and mannitol at a concentration of about 250-260 mM; pH 6.5;

- Amylin analogue at a concentration of about 2.4 mg/ml, citrate buffer at a concentration of about 10 mM, and mannitol at a concentration of about 250-260 mM; pH 6.5;
- Amylin analogue at a concentration of about 4.5 mg/ml, citrate buffer at a concentration of about 10 mM, and mannitol at a concentration of about 250-260 mM; pH 6.5;
- Amylin analogue at a concentration of about 9 mg/ml, citrate buffer at a concentration of about 10 mM, and mannitol at a concentration of about 250-260 mM; pH 6.5.

These formulations may be particularly suitable for a dosing volume of 1.0 ml, although it will be understood that they may be used for other dosing volumes. Alternatively, the concentration of amylin analogue may be adjusted for a different dosing volume.

In these formulations, as elsewhere, the amylin analogue be provided as a chloride salt, e.g. having the formula:

(SEQ ID NO: 3)
([19CD]-isoGlu-RD( )GTATK( )ATERLA-Aad-FLQRSSF-Gly(Me)-A-Ile(Me)-LSSTEVGSNT-Hyp-$NH_2$), x(Cl)

where x is 1.0-2.0.

The invention further provides a container or delivery device containing a stable aqueous liquid formulation as described herein. By way of example, suitable containers and delivery devices include a sealed vial, a pre-filled syringe, or a cartridge for an injector device such as an injector pen, an adjustable dose auto-injector, a disposable auto-injector, a wearable injector, or an infusion pump. The delivery device may be a single-use device, such as a pre-filled syringe.

In a further aspect, the present invention provides an article of manufacture or a kit comprising a container holding a stable aqueous liquid pharmaceutical composition of the invention.

The present invention further provides a stable aqueous liquid formulation as described for use in a method of medical treatment.

The formulations are useful, inter alia, in the reduction of food intake, promotion of weight loss, and inhibition or reduction of weight gain. As a result, they may be used for treatment of a variety of conditions, diseases, or disorders in a subject, including, but not limited to, obesity and various obesity-related conditions, diseases, or disorders, such as diabetes (e.g. type 2 diabetes), hypertension, dyslipidemia, sleep apnea and cardiovascular disease. The subject may be affected by obesity accompanied by at least one weight-related co-morbid condition, such as diabetes (e.g. type 2 diabetes), hypertension, dyslipidemia, sleep apnea and cardiovascular disease. It will be understood that the formulations may thus be administered to subjects affected by conditions characterised by inadequate control of appetite or otherwise over-feeding, such as binge-eating disorder and Prader-Willi syndrome. It will be clear that the formulations can be used for treatment of combinations of the conditions described.

Thus, the invention provides a formulation of the invention for use in a method of treating, inhibiting or reducing weight gain, promoting weight loss and/or reducing excess body weight. Treatment may be achieved, for example, by control of appetite, feeding, food intake, calorie intake and/or energy expenditure.

The invention also provides a formulation of the invention for use in a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility. The subject may be affected by obesity accompanied by at least one weight-related co-morbid condition, such as diabetes (e.g. type 2 diabetes), hypertension, dyslipidemia, sleep apnea and cardiovascular disease.

The invention also provides a formulation of the invention for use in a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart disease (including diabetic cardiomyopathy and heart failure as a diabetic complication), coronary heart disease, peripheral artery disease or stroke, and combinations thereof.

The invention also provides a formulation of the invention for use in a method of lowering circulating LDL levels and/or increasing HDL/LDL ratio.

Effects of the formulations on these conditions may be mediated in whole or in part via an effect on body weight, or may be independent thereof.

The invention further provides use of a formulation of the invention in the manufacture of a medicament for treating, inhibiting or reducing weight gain, promoting weight loss and/or reducing excess body weight.

The invention also provides use of a formulation of the invention in the manufacture of a medicament for treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility. The subject may be affected by obesity accompanied by at least one weight-related co-morbid condition, such as diabetes (e.g. type 2 diabetes), hypertension, dyslipidemia, sleep apnea and cardiovascular disease.

The invention also provides use of a formulation of the invention in the manufacture of a medicament for the prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart disease (including diabetic cardiomyopathy and heart failure as a diabetic complication), coronary heart disease, peripheral artery disease or stroke, and combinations thereof.

The invention also provides use of a formulation of the invention in the manufacture of a medicament for lowering circulating LDL levels and/or increasing HDL/LDL ratio.

The invention further provides a method of treating, inhibiting or reducing weight gain, promoting weight loss and/or reducing excess body weight in a subject, comprising administering a therapeutically effective amount of a formulation of the invention to the subject.

The invention also provides a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility in a subject, comprising administering a therapeutically effective amount of a formulation of the invention to the subject. The subject may be affected by obesity accompanied by at least one weight-related co-morbid condition, such as diabetes (e.g. type 2 diabetes), hypertension, dyslipidemia, sleep apnea and cardiovascular disease.

The invention also provides a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart disease (including diabetic cardiomyopathy and heart failure as a diabetic complication), coronary heart disease, peripheral artery disease or stroke, and combinations thereof, in a subject, comprising administering a therapeutically effective amount of a formulation of the invention to the subject.

The invention further provides a method of lowering circulating LDL levels and/or increasing HDL/LDL ratio in a subject, comprising administering a therapeutically effective amount of a formulation of the invention to the subject.

The invention further provides the use of a formulation as described above in a method of cosmetic (i.e. non-therapeutic) weight loss.

It will be understood that references to therapeutic uses of formulation and methods comprising administration of formulation may equally be taken to encompass cosmetic uses and administration.

The invention further provides a process for producing a stable aqueous pharmaceutical formulation comprising an amylin analogue, which is:

(SEQ ID NO: 3)
[19CD]-isoGlu-RD( )GTATK( )ATERLA-Aad-FLQRSSF-

Gly(Me)-A-Ile(Me)-LSSTEVGSNT-Hyp-$NH_2$ or a pharmaceutically acceptable salt and/or derivative thereof;

the process comprising formulating (a) the amylin analogue, salt or derivative, at a concentration of from about 0.4 mg/ml to about 25 mg/ml; and (b) a buffer at a concentration of about 0.5 mM to about 25 mM;

to produce the stable aqueous liquid formulation, wherein the formulation has a pH of wherein the formulation has a pH of about 5.8 to about 6.9.

It will be apparent that the process may be applied to any of the formulations of the invention described herein.

Thus, for example, the process may further comprise formulating the amylin analogue and buffer with a tonicity modifier as described.

The process may comprise a step of adjusting the pH to the desired value. When the tonicity modifier is a chloride salt, e.g. NaCl, it may be desirable to adjust the pH to the desired value before adding the tonicity modifier to the formulation. This may particularly be the case where the amylin analogue is itself provided in the form of a chloride salt, since the presence of chloride ions above a certain level may promote precipitation or fibrillation of the amylin analogue at pH values around the pI of the peptide (pI=4.36).

Also provided is a formulation produced by the process described.

Unless context dictates otherwise, the descriptions and definitions of the features set out above are not limited to any particular aspect or embodiment of the invention and apply equally to all aspects and embodiments which are described.

Throughout this specification, the term "about" in relation to a numerical value is optional and means, for example, +/−10%.

DETAILED DESCRIPTION OF THE INVENTION

Throughout the description and claims the conventional one-letter and three-letter codes for natural amino acids are used. All amino acid are of the L-configuration unless stated otherwise.

Amylin Analogue

The amylin analogue (Compound 1; "CPD 1") present in the formulations of the present invention is described in WO 2018/046719 and has the formula:

(SEQ ID NO: 3)
[19CD]-isoGlu-RD( )GTATK( )ATERLA-Aad-FLQRSSF-

Gly(Me)-A-Ile(Me)-LSSTEVGSNT-Hyp-$NH_2$,

Gly(Me): N-methylglycine [also known as sarcosine (Sar)]

Ile(Me): N-methylisoleucine

Aad: 2-aminoadipic acid, e.g. (2S)-2-aminoadipic acid [also (2S)-2-aminohexanedioic acid], also known as homo-glutamic acid

[19CD]-: 19-carboxy-nonadecanoyl-

Parentheses "( )" shown after the symbols for particular amino acid residues indicate residues whose side chains participate in an intramolecular lactam bridge. Thus, the amylin analogue compound present in the formulations of the invention has an intramolecular lactam bridge formed between the side chains of the residues (aspartic acid and lysine respectively) indicated by parentheses.

The term "isoGlu" is used to refer to a glutamic acid residue which participates in bonds via its side chain carboxyl group and its alpha amino group. It may also be designated γ-Glu.

Thus, [19CD]-isoGlu- indicates a 19-carboxy-nonadecanoyl group covalently attached to the alpha amino group of the Glu linker via an amide linkage. The side chain carboxyl group of the Glu linker is in turn linked via an amide linkage to the backbone alpha-amino group of the arginine residue at the N-terminus of the amylin analogue peptide chain.

The formula below illustrates this configuration, including the side chain and carbonyl oxygen of the N-terminal arginine residue:

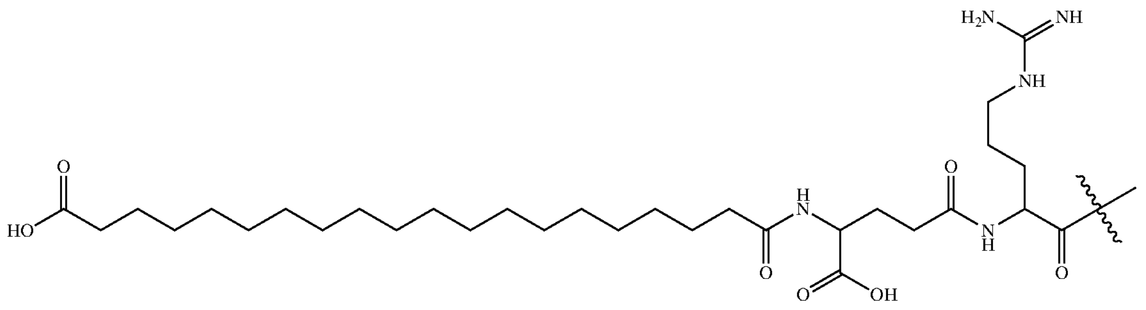 [SMILES: *C(=O)C(CCCNC(=N)N)NC(=O)CCC(NC(=O)CCCCCCCCCCCCCCCCCCC(=O)O)C(=O)O]

It should be understood that the amylin analogue (active substance) might also be provided in the form of a salt or other derivative. Salts are typically "pharmaceutically acceptable" salts which, in the context of the invention, refers to a salt that is not harmful to the patient or subject to be treated therewith. Such salts are in general acid addition salts or basic salts. Acid addition salts include salts of inorganic acids and salts of organic acids. Non-limiting examples of suitable acid addition salts include hydrochloride salts, phosphate salts, formate salts, acetate salts, trifluoroacetate salts and citrate salts. Examples of basic salts include salts where the cation is selected from alkali metal ions, such as sodium and potassium, alkaline earth metal ions, such as calcium, as well as substituted ammonium ions, e.g. of the type $$NR(R')_3^+,$$

where R and R' independently designate optionally substituted $C_{1-6}$alkyl, optionally substituted $C_{2-6}$alkenyl, optionally substituted aryl, or optionally substituted heteroaryl. Other examples of pharmaceutically acceptable salts are described in Remington's Pharmaceutical Sciences, 17th edition. Ed. Alfonso R. Gennaro (Ed.), Mack Publishing Company, Easton, PA, U.S.A., 1985 and more recent editions, and in the Encyclopaedia of Pharmaceutical Technology.

In particular, the salt may be a chloride salt. In some embodiments, the amylin analogue may have the formula (SEQ ID NO: 3)
([19CD]-isoGlu-RD( )GTATK( )ATERLA-Aad-FLQRSSF- Gly(Me)-A-Ile(Me)-LSSTEVGSNT-Hyp-$NH_2$), x(Cl)
where x is 1.0-2.0.

Other derivatives of the amylin analogues include coordination complexes with metal ions such as $Mn^{2+}$ and $Zn^{2+}$, esters such as in vivo hydrolysable esters, free acids or bases, hydrates, prodrugs or lipids. Esters can be formed between hydroxyl or carboxylic acid groups present in the compound and an appropriate carboxylic acid or alcohol reaction partner, using techniques well known in the art. Derivatives which as prodrugs are convertible in vivo or in vitro into one of the parent compounds. Typically, at least one of the biological activities of the compound will be reduced in the prodrug form of the compound, and can be activated by conversion of the prodrug to release the compound or a metabolite of it. Examples of prodrugs include the use of protecting groups which may be removed in situ releasing active compound or serve to inhibit clearance of the drug in vivo.

The amylin analogue is an amylin receptor agonist, and has agonist activity at the receptors hAMYR1, hAMYR2 and hAMYR3 (human amylin receptors 1, 2 and 3) as described in WO 2018/046719. Binding to a suitable receptor induces intracellular signalling, e.g. cyclic AMP production. In vivo, the amylin analogue has the biological activity of (inter alia) reducing food intake, promoting weight loss, and/or inhibiting or reducing weight gain. It may be employed for various therapeutic applications as described elsewhere in this specification and in WO 2018/046719.

Aqueous Liquid Formulation

Preferably the formulations of the present invention substantially do not include organic solvent. In particular preferred embodiments, water is the sole solvent used to make the aqueous liquid formulation.

The formulations of the invention are aqueous liquid formulations, i.e. formulations comprising water, in the form of an aqueous solution. In the context of the invention the term "aqueous formulation" will normally refer to a formulation comprising at least 50% by weight (50% w/w) of water as a solvent, more preferably at least 75% w/w of water, more preferably at least 80% w/w of water, more preferably at least 85% w/w of water, more preferably at least 90% w/w of water, most preferably at least 95% w/w of water. In certain embodiments, aqueous formulations of the present invention substantially do not include organic solvents, such as aprotic polar solvents such as dimethyl sulfoxide (DMSO). "Substantially" in this sense means that the aqueous formulations include less than 5% by volume organic solvent, more preferably less than 2% by volume (v/v) organic solvent and even more preferably less than 1% by volume (v/v) organic solvent. In preferred embodiments, no organic solvent is present. Thus, typically, water is the sole solvent used to make the aqueous liquid formulations.

The components and amounts of the liquid formulations of the present invention are chosen to provide a formulation with a pH of about 5.8 to about 6.9, e.g. a pH of about 6.2 to about 6.8, e.g. about 6.4 to about 6.6, e.g. about 6.5. For the avoidance of doubt, pH is measured at 25° C.

The formulations of the present invention may further comprise a preservative, especially when it provided in a multi-use format. Alternatively, and especially when provided in single-use format, the formulation may contain no or substantially no preservative. When a preservative is present, it will be employed in an amount effective to kill a range of bacterial types as required for regulatory approval. Suitable preservatives include meta-cresol, phenol, methylparaben, ethylparaben, propylparaben, butylparaben, chlorobutanol, benzyl alcohol, phenylmercuric nitrate, thimerosal, sorbic acid, potassium sorbate, benzoic acid, chlorocresol and benzalkonium chloride. The preservative will be present in an amount effective to kill a range of bacterial types as required for regulatory approval.

The formulations of the invention are suitable for parenteral administration, typically by injection. Thus administration may, for example, be by subcutaneous, intramuscular, intraperitoneal or intravenous injection, although subcutaneous administration may be preferred.

The formulations of the invention may be provided in a container or delivery device. In some embodiments, the container or delivery device is for single use. In other embodiments, the container or delivery device is for multi-use.

Examples include a sealed vial, a pre-filled syringe, and an injector device such as an injector pen, an adjustable dose auto-injector, a disposable auto-injector, a wearable injector, or an infusion pump.

Stability

A "stable" formulation is one in which the peptide therein essentially retains its physical stability and/or chemical stability and/or biological activity upon storage. Preferably, the formulation essentially retains its physical and chemical stability, as well as its biological activity, upon storage. The storage period is generally selected based on the intended shelf-life of the formulation. Various analytical techniques for measuring protein stability are available in the art and are reviewed in *Peptide and Protein Drug Delivery,* 247-301, Vincent Lee Ed., Marcel Dekker, Inc., New York, N.Y., Pubs. (1991) and Jones, A. *Adv. Drug Delivery Rev.* 10: 29-90 (1993), for example. The chemical and physical stability of the amylin analogue in any given formulation can be determined according to the assays outlined in the Examples below.

The aqueous liquid formulation is typically stable for at least 6 months, e.g. at least 12 months, at least 18 months or at least 24 months, at 2-8° C. (e.g. at 5° C.). Preferably it is stable for at least 18 months, e.g. at least 24 months, at 2-8° C. (e.g. at 5° C.).

It is also possible to test stability under accelerated or extreme conditions, which generally use an increased storage temperature in order to assess stability over reduced time periods. For example, storage at 25° C. (sometimes referred to as "accelerated conditions at 25° C." or simply "accelerated conditions") may be used to assess stability over a shorter period, e.g. of 1, 2, 3 or 4 weeks, 1 month, 2 months, 3 months, or 6 months.

The term "physical stability" as used herein refers to a measure of the tendency of the amylin analogue to form soluble or insoluble aggregates, e.g. fibrils.

Physical stability (e.g. turbidity of the solution, or aggregation, fibrillation or gelling of the amylin analogue) can be evaluated qualitatively and/or quantitatively in a variety of different ways, e.g. by visual inspection, by using size exclusion chromatography, UV light scattering, dynamic light scattering (DLS), circular dichroism, by measuring turbidity, or using a spectroscopic probe (such as Thioflavin T) that indicates the conformational status of the peptide. The probe is preferably a small molecule that preferentially binds to a non-native conformer of the peptide. Thioflavin T (ThT) is a fluorescent dye that has been widely used for the detection of amyloid fibrils. In the presence of fibrils, and perhaps also other peptide configurations, Thioflavin T gives rise to a new excitation maximum at about 450 nm and enhanced emission at about 482 nm when bound to a fibril form of a peptide. Unbound Thioflavin T is essentially non-fluorescent at the wavelengths in question.

In some embodiments, the formulation displays substantially no changes indicative of reduced physical stability (e.g. as demonstrated by turbidity of the solution, or of aggregation, fibrillation or gelling of the amylin analogue) after it has been stored at 2-8° C. (e.g. at 5° C.) for at least 6 months, at least 12 months, at least 18 months, or at least 24 months. Preferably, the formulation displays substantially no such changes after it has been stored at 2-8° C. (e.g. at 5° C.) for at least 18 months, e.g. at least 24 months.

Additionally or alternatively, the formulation may display substantially no such changes after storage under accelerated conditions (25° C.) for a period of 1, 2, 3 or 4 weeks, 1 month, 2 months, 3 months, or 6 months.

The term "chemical stability" as used herein refers to stability of a peptide with respect to covalent/chiral chemical changes in the peptide structure that lead to formation of chemical degradation products and/or covalent oligomers with potentially lower biological potency compared to the original intact monomeric peptide structure. The primary degradation product from the amylin analogue present in the formulations of the invention is believed to result from deamidation of the asparagine side chain and/or the C-terminal amide group to form free carboxylic acid groups. Covalently-linked oligomers may also form in sub-optimal formulations.

The chemical stability of a formulation may be evaluated by measuring the amount of intact monomeric peptide remaining, of particular chemical degradation products, or of covalent oligomers, at various time-points after exposure to different environmental conditions. The amount of each individual degradation product may be determined by separation of the degradation products to generate a "degradation profile". However, the amount of remaining intact monomeric peptide may be the preferred indicator of chemical stability. The separation is usually done on the basis of molecular size and/or charge using various chromatographic techniques such a size exclusion chromatography (SEC) or reverse phase (RP) chromatography, typically using high performance liquid chromatography (HPLC), e.g. SEC-HPLC (Size Exclusion Chromatography HPLC) and/or RP-HPLC (Reversed Phase HPLC)).

In some embodiments, at least 80%, more preferably at least 85%, at least 90%, at least 95%, at least 96%, at least 97%, at least 98%, or at least 99% of the amylin analogue remains in intact monomeric in the formulation after it has been stored at 2-8° C. (e.g. at 5° C.) for at least 6 months, at least 12 months, at least 18 months, or at least 24 months. Preferably, at least 90%, at least 95%, at least 96%, at least 97%, at least 98%, or at least 99% of the amylin analogue remains in intact monomeric form in the formulation after it has been stored at 2-8° C. (e.g. at 5° C.) for at least 6 months, at least 12 months, at least 18 months, or at least 24 months. More preferably, at least 90%, at least 95%, at least 96%, at least 97%, at least 98%, or at least 99% of the amylin analogue remains in intact monomeric form in the formulation after it has been stored at 2-8° C. (e.g. at 5° C.) for at least 18 months, e.g. at least 24 months.

Buffer

The term "buffer" as used herein denotes a pharmaceutically acceptable agent which stabilizes the pH of a pharmaceutical formulation. Suitable buffers are well known in the art and can be found in the literature.

Any suitable buffer may be used, including a phosphate buffer, histidine buffer, TRIS (tris(hydroxymethyl)aminomethane) buffer, acetate buffer, arginine buffer, citrate buffer, bicarbonate buffer, diethanolamine buffer, lysine buffer and TAPS ([tris(hydroxymethyl)methylamino]propanesulfonic acid) buffer. Particularly preferred buffers include phosphate buffer, histidine buffer, citrate buffer and TRIS buffer, especially phosphate buffer, histidine buffer and citrate buffer.

Surprisingly, stability was found to be increased at relatively low buffer concentrations. Thus the buffer is present at a concentration of about 0.5 mM to about 25 mM.

The buffer may be present at a concentration of about 0.5 mM to about 20 mM, e.g. about 0.5 mM to about 15 mM, e.g. about 1 mM to about 15 mM, e.g. about 1 mM to about 12 mM. For example, it may be present at a concentration of about 3 mM to about 7 mM or about 8 mM to about 12 mM, e.g. about 5 mM or about 10 mM.

For TRIS buffer, it may be preferred to be present at about 15 mM to about 25 mM, e.g. about 17 mM to about 23 mM, e.g. about 20 mM, since the buffering capacity of TRIS is lower than that of other buffers such as (e.g.) phosphate, histidine and citrate.

It may be possible for the formulation to contain more than one buffer, e.g. two buffers, or even more. In such cases, the quoted concentration may represent the sum of the concentrations of the individual buffers. For example, a formulation containing 2.5 mM phosphate buffer and 2.5 mM histidine buffer may be considered to contain 5 mM buffer overall.

Tonicity Modifier

The term "tonicity modifier" as used herein denotes pharmaceutically acceptable tonicity agents that are used to modulate the tonicity of the formulation. The terms "tonicity modifier" and "tonicity agent" may be used interchangeably. The formulations of the present invention are preferably isosmotic, that is they have an osmotic pressure that is substantially the same as human blood serum, e.g. about 300+/−80 mOsm, e.g., e.g. 300+/−60 mOsm, as measured by an osmometer.

The tonicity modifier may be ionic or non-ionic. Suitable ionic tonicity modifiers include alkali metal salts (e.g. halides) and earth metal salts (e.g. halides), such as NaCl, NaBr, NaI, KCl, KBr, KI, LiCl, $CaCl_2$ and $Na_2SO_4$. Non-ionic tonicity modifiers include mannitol (e.g. D-mannitol), propylene glycol, sucrose, glycerol, sorbitol, trehalose and dextrose.

Where the tonicity modifier is a chloride salt, such as NaCl, it may be desirable that the tonicity modifier is only added to the formulation once the pH has been adjusted to the desired value. This may particularly be the case where the amylin analogue is itself provided in the form of a chloride salt, since the presence of chloride ions above a certain level may promote precipitation or fibrillation of the amylin analogue at pH values around the pI of the peptide (pI=4.36).

In some embodiments, mannitol (e.g. D-mannitol), propylene glycol and NaCl may be preferred as tonicity modifiers, especially mannitol (e.g. D-mannitol) and propylene glycol.

It will be understood that the concentration of the tonicity modifier will be dependent on the concentration of other components of the formulation, especially where the formulation is intended to be isosmotic. The skilled person is capable of establishing the appropriate concentration for any given agent, in the context of a specific formulation.

For example, it may be appropriate to employ mannitol in a concentration of 200-300 mM, e.g. 230-260 mM; it may be appropriate to employ propylene glycol in a concentration of 200-250 mM, e.g. 224 mM; it may be appropriate to employ NaCl in a concentration of 100-150 mM, e.g. 118-137 mM.

Therapeutic Uses

The formulations of the invention are useful, inter alia, in the reduction of food intake, promotion of weight loss, and inhibition or reduction of weight gain. They may therefore provide an attractive treatment option for, inter alia, obesity and metabolic diseases caused, characterised by, or associated with, excess body weight.

Thus, the formulations may be used in a method of treating, inhibiting or reducing weight gain, promoting weight loss, reducing food intake, and/or reducing excess body weight. Treatment may be achieved, for example, by control of appetite, feeding, food intake, calorie intake and/or energy expenditure.

The formulations may be used in a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility.

The formulations may also be used in in a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart disease (including diabetic cardiomyopathy and heart failure as a diabetic complication) coronary heart disease, peripheral artery disease or stroke.

The formulations may also be useful in lowering circulating LDL levels and/or increasing HDL/LDL ratio.

These effects may be mediated in whole or in part via an effect on body weight, or may be independent thereof.

Metabolic syndrome is characterized by a group of metabolic risk factors in one person. They include abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension), insulin resistance and glucose intolerance, prothrombotic state (e.g. high fibrinogen or plasminogen activator inhibitor-1 in the blood), and proinflammatory state (e.g., elevated C-reactive protein in the blood).

Individuals with metabolic syndrome are at increased risk of coronary heart disease and other diseases related to other manifestations of arteriosclerosis (e.g. stroke and peripheral vascular disease). The dominant underlying risk factor for this syndrome appears to be abdominal obesity.

The term "treatment" (as well as "treating" and other grammatical variants thereof) as employed in the context of the invention refers to an approach for obtaining beneficial or desired clinical results. For the purposes of the present invention, beneficial or desired clinical results include, but are not limited to, alleviation of symptoms, diminishment of extent of disease, stabilization of (i.e. not worsening of) state of disease, delay or slowing of disease progression, amelioration or palliation of disease state, and remission (whether partial or total), whether detectable or undetectable. “Treatment” may also refer to prolongation of survival compared to expected survival in the absence of treatment. “Treatment” is an intervention performed with the intention of preventing the development of, or altering the pathology of, a disorder. Accordingly, “treatment” refers both to therapeutic treatment and to prophylactic or preventative measures. As used in the context of prophylactic or preventative measures, the pharmaceutical formulation need not completely prevent the development of the disease or disorder. Those in need of treatment include those already suffering from the disorder, as well as those in which development of the disorder is to be prevented. “Treatment” also means inhibition or reduction of an increase in pathology or symptoms (e.g. weight gain or hypoglycaemia) compared to the absence of treatment, and is not necessarily meant to imply complete cessation of the relevant condition.

EXAMPLES

The following examples are provided to illustrate preferred aspects of the invention and are not intended to limit the scope of the invention.

Methods

Preparation of Compound 1 (CPD 1) Formulations (METHOD 1)

Compound 1 (described in WO 2018/046719) was prepared as a chloride salt.

Except where noted below, formulations of CPD 1 were prepared by dissolving CPD 1 peptide in alkaline MilliQ water (MQW) (pH adjusted with NaOH) to generate a clear drug substance (DS) stock solution at approximately pH 7 at a concentration relevant for target end-product concentration. Relevant excipients were dissolved in MQW at appropriate pH to form an excipient solution. The two solutions were mixed, and pH was measured and, if necessary, adjusted using diluted NaOH/HCl as needed to reach the desired pH. Finally, appropriate amount of MQW was added to reach end-product concentration. The formulation was sterile filtered through a 0.22 μm filter and filled in suitable containers.

Method for Determining Chemical Stability (ASSAY 11)

The following methods were used to assess chemical stability of CPD 1.

Determination of Purity (%) by RP-HPLC (ASSAY IIa)

A Dionex Ultimate 3000 HPLC system, at a flow rate of 0.3 mL/min was used for the analysis. The mobile phase components consisted of 20 mM phosphate buffer, pH 7.0 with gradient elution in acetonitrile (ACN). A wavelength of 220 nm was used for detection. Injection amount was 4 μg of peptide. The column used for HPLC analysis was a Waters Acquity UPLC BEH C18, 150 by 2.1 mm, 1.7 μm particle size. Runtime was 35 to 37 minutes depending on reconditioning time.

The results shown in the examples are measured by RP-HPLC after incubation under stress conditions. The chemical stability of the CPD 1 (peptide) is herein expressed as the relative purity of the peptide peak (i.e. the main peptide peak) determined by HPLC at a given time point, and normalized to the absolute purity of the peptide peak (i.e. main peptide peak) at day zero (day 0 (D0)), which is set to 100% purity and thus chemical stability expressed in % of CPD 1.

Purity is a measure for the remaining intact compound in stressed solutions after incubation, relative to the purity measured on day 0 (DO, day zero) and expressed as the normalized CPD 1 purity in %.

Determination of Covalent Oligomer Formation by Size Exclusion Chromatography (SEC) (ASSAY IIb)

A Dionex Ultimate 3000 HPLC system, at a flow rate of 0.5 mL/min (isocratic elution) was used for the analysis. The mobile phase components consisted of 0.1% trifluoroacetic acid (TFA) in 45% acetonitrile (ACN) and 55% MQW. A wavelength of 215 nm (+280 nm) was used for detection. Injection amount was 4 μg of peptide. The column used for HPLC analysis was a Tosoh BioScience, TSKgel SuperSW2000, 30 cm by 4.6 mm, 4 μm particle size. Runtime was 25 minutes.

The results shown in the examples are measured by HPLC after incubation under stress conditions. Level of covalent oligomer is calculated as the peak area of the covalent oligomer, relative to the intact monomeric main peak of CPD 1, expressed as % oligomers.

Methods for Assessment of Physical Stability (ASSAY III)

The following methods were used to assess physical stability of CPD 1 in formulations.

Visual Inspection of the Solution (ASSAY IIIa)

The sample is provided in a transparent container allowing the formulation to be inspected visually by trained and experienced technicians. The visual inspection was performed manually and documented by experienced technicians, who classified the sample as “clear”, “turbid”, “gel” or “particles” depending on its appearance.

UV-Absorbance at 325 nm (ASSAY IIIb)

Turbidity was measured with UV absorbance analysis. 100 μL of each sample is loaded into a clear 96 well UV compatible plate from Corning. Samples are measured in a SpectraMax 190 Elisa reader at 325 nm.

Dynamic Light Scattering (DLS) (ASSAY IIIc)

Peptide particle size distribution was determined with dynamic light scattering analysis. The standard DLS experiment is conducted in a nunc 96 well plate with a sample volume of 165 μL and measured in a DynaPro Plate reader II instrument. Typically used parameters were temperature at 25° C., acquisition time 2 s, 50 acquisitions per sample, Detection: Hydrodynamic radius Rh, Correlation function cut off [μs]: 0.5-1×105 and Peak radius cut off [nm]: 0.5-1000.

Physical Stability Evaluation by ThT-Stress Test (ASSAY IIId)

Aggregation in the form of fibril formation was detected using the amyloid-specific dye Thioflavin T (ThT), which is frequently employed to demonstrate the presence of fibrils in solution (see, e.g., Groenning, M., *J. Chem. Biol.* 3(1) (2010), pp. 1-18; Groenning et al., *J. Struct. Biol.* 158 (2007) pp. 358-369; and Levine, H., III, *Protein Sci.* 2 (1993) pp. 404-410).

A 1 mM ThT stock solution was prepared and 12 μL was mixed with 288 μL of CPD 1 formulation. Samples were loaded in a 96-well black fluorescence plate (clear bottom) in duplicate 2×150 μL. Data were collected in a Fluorescence Plate reader from Biotek Synergy™ H4 Hybrid Multi-Mode at fixed intervals of 10 min, each preceded by 300 s of auto mixing (agitation), over a period of up to 60 hours at 40° C. Physical stability, expressed as lag-time of fibril formation (in hours), was defined as the intersection between two linear regressions representing the initial stable phase and the growth phase.

Physical Stability Evaluation by ThT-One Point (ASSAY IIIe)

Aggregation in the form of fibril formation was detected using the amyloid-specific dye Thioflavin T (ThT), which is frequently employed to demonstrate the presence of fibrils in solution (see, e.g., Groenning, M., J. Chem. Biol. 3(1) (2010), pp. 1-18; Groenning et al., J. Struct. Biol. 158 (2007) pp. 358-369; and Levine, H., III, Protein Sci. 2 (1993) pp. 404-410).

170 μL of CPD 1 formulation sample was loaded into a black 96 well plate with optical bottom from Nunc. Additional 7 μL 1 mM ThT was added and mixed by gently pipette up and down to ensure homogenous dispersion of ThT. The 96 well plate was placed in the Fluorescence Plate reader Biotek Synergy™ H4 Hybrid Multi-Mode or Fluorescence Plate reader Biotek Synergy™ MX. Excitation 450 nm (bandwidth 9 nm) with Emission 485 nm (bandwidth 9 nm) and Excitation 295 nm (bandwidth 9 nm) with Emission 355 nm (bandwidth 9 nm) and Emission 330 nm (bandwidth 9 nm).

Example 1: Accelerated Chemical and Physical Stability at 25° C. Of Formulations in pH Range 6.1-7.8

Formulations described in Table 1 were prepared as described in METHOD I, except as stated in the table:

TABLE 1

| # | CPD 1 (mg/ml) | Buffer | Tonicity agent | pH | Notes |
|---|---|---|---|---|---|
| 1 | 4 | Phosphate 5 mM | Mannitol 230 mM | 6.1 | CPD 1 DS dissolved in a mixture of MQW and diluted HCl at pH 3 and pH subsequently adjusted with diluted NaOH to reach appropriate pH in the DS stock solution.ani |
| 2 | 4 | Phosphate 5 mM | Mannitol 230 mM | 6.5 | CPD 1 DS dissolved in a mixture of MQW and diluted HCl at pH 3. pH was not adjusted prior to addition of excipient stock solution. |
| 3 | 4 | TRIS 20 mM | NaCl 118 mM | 6.9 | CPD 1 DS dissolved in MQW at pH 3 and pH subsequently adjusted with diluted NaOH to reach appropriate pH in the DS stock solution. |
| 4 | 4 | Phosphate 5 mM | NaCl 125 mM | 7.3 | None |
| 5 | 1 | No buffer | NaCl 154 mM | 7.8 | None |

The prepared formulations were filled into 1 ml Type 1 glass vials and analysed after storage protected from light at 25° C. for the time periods indicated.

TABLE 2

| # | Parameter | t = 0 | 1 M | 2 M | 3 M | 6 M |
|---|---|---|---|---|---|---|
| 1 | Purity (RP-HPLC) | 100% | No data | 98.9% | No data | 95.9% |
| | Covalent oligomers (SEC) | 0.07% | 0.15% | 0.17% | 0.13% | 0.27% |
| | Visual inspection | Clear | Clear | Clear | Clear | Clear |
| | Physical stability[1] | No signs of aggregation | No change | No change | No change | No change |
| 2 | Purity (RP-HPLC) | 100% | No data | 98.3% | 98.0% | 95.2% |
| | Covalent oligomers (SEC) | 0.08% | 0.15% | 0.15% | 0.16% | 0.19% |
| | Visual inspection | Clear | Clear | Clear | Clear | Clear |
| | Physical stability[1] | No signs of aggregation | No change | No change | No change | No change |
| 3 | Purity (RP-HPLC) | 100% | No data | 95.5% | 93.8% | 86.6% |
| | Covalent oligomers (SEC) | 0.08% | 0.14% | 0.13% | 0.13% | 0.15% |
| | Visual inspection | Clear | Clear | Clear | Clear | Clear |
| | Physical stability[1] | No signs of aggregation | No change | No change | No change | No change |
| 4 | Purity (RP-HPLC) | 100% | 97.5% | 94.4% | 90.5% | 85.9% |
| | Covalent oligomers (SEC) | 0.07% | 0.12% | 0.13% | No data | 0.15% |
| | Visual inspection | Clear | Clear | Clear | No data | Clear |
| | Physical stability[1] | No change | No change | No change | No data | No change |
| 5 | Purity (RP-HPLC) | 100% | No data | 91.6% | 88.0% | 71.7 |
| | Covalent oligomers (SEC) | 0.06% | No data | 0.05% | 0.09% | No data % |
| | Visual inspection | Clear | Clear | Clear | Clear | Clear |
| | Physical stability[1] | No signs of aggregation | No change | No change | No change | No change |

[1]ThT-one point, UV absorbance at 325 nM, or DLS;

M: Month

While there is no clear effect of pH on physical stability, purity is increasing with decreasing pH, see Table 2.

Example 2: Effect of Formulation pH on Physical Stability

CPD 1 drug product formulations were prepared as described in METHOD I at pH 5.8, 6.0, 6.3, 6.8 and 7.0, containing 1 mg/ml CPD 1, 20 mM TRIS (buffer) and 118 mM NaCl (tonicity agent).

Physical stability was evaluated in terms of fibril formation by ThT-stress test measured over 60 hours at 40° C. Initial peptide particle size (z-average) was also determined by DLS.

TABLE 3

| | pH | | | | | |
|---|---|---|---|---|---|---|
| | 5.8 | 6.0 | 6.3 | 6.6 | 6.8 | 7.0 |
| ThT lag time (h) | >60 | >60 | >60 | >60 | >60 | >60 |
| Peptide particle size (nm) | 3.3 | 4.0 | 3.2 | 3.0 | 3.7 | 3.0 |

Table 3 shows that in the pH range 5.8-7.0, CPD 1 is stable towards fibrillation and aggregation impacting peptide particle size.

Example 3: Accelerated Chemical and Physical Stability at 25° C. For Formulations with Buffer Concentrations from 2 mM to 20 mM Formulations described in Table 4 were prepared as described in METHOD I. The prepared formulations were filled into 1 ml Type 1 glass vials and analysed after storage protected from light at 25° C. for the time periods indicated.

TABLE 4

| # | CPD 1 (mg/ml) | Buffer | Tonicity agent | pH | Parameter | t = 0 | 1 M | 2 M | 3 M | 6 M |
|---|---|---|---|---|---|---|---|---|---|---|
| 1 | 1 | Phosphate 20 mM | Mannitol 230 mM | 6.6 | Purity (RP-HPLC) | 100% | 98.6% | 97.8% | No data | No data |
| | | | | | Covalent oligomers (SEC) | 0.08% | 0.11% | 0.11% | 0.12% | 0.28% |
| | | | | | Visual inspection | Clear | Clear | Clear | Clear | Clear |
| | | | | | Physical stability[1] | NSA[2] | No change | No change | No change | No change |
| 2 | 1 | Phosphate 5 mM | Mannitol 230 mM | 6.5 | Purity (RP-HPLC) | 100% | 99.4% | 98.8% | 97.4% | 95.8% |
| | | | | | Covalent oligomers (SEC) | 0.08% | 0.11% | 0.09% | 0.11% | 0.40% |
| | | | | | Visual inspection | Clear | Clear | Clear | Clear | Clear |
| | | | | | Physical stability[1] | NSA[2] | No change | No change | No change | No change |
| 3 | 1 | Histidine 20 mM | Mannitol 230 mM | 6.6 | Purity (RP-HPLC) | 100% | 98.4% | 97.1% | 94.6% | 90.9% |
| | | | | | Covalent oligomers (SEC) | 0.09% | 0.12% | 0.12% | 0.11% | 0.26% |
| | | | | | Visual inspection | Clear | Clear | Clear | Clear | Clear |
| | | | | | Physical stability[1] | NSA[2] | No change | No change | No change | No change |
| 4 | 1 | Histidine 5 mM | Mannitol 230 mM | 6.7 | Purity (RP-HPLC) | 100% | 99.1% | 98.4% | 95.8% | 93.8% |
| | | | | | Covalent oligomers (SEC) | 0.08% | 0.12% | 0.10% | 0.14% | 0.17% |
| | | | | | Visual inspection | Clear | Clear | Clear | Clear | Clear |
| | | | | | Physical stability[1] | NSA[2] | No change | No change | No change | No change |
| 5 | 4 | TRIS 20 mM | NaCl 120 mM | 6.9 | Purity (RP-HPLC) | 100% | 98.3% | 97.0% | 93.8% | No data |
| | | | | | Covalent oligomers (SEC) | 0.07% | 0.11% | 0.12% | No data | No data |
| | | | | | Visual inspection | Clear | Clear | Clear | Clear | Clear |
| | | | | | Physical stability[1] | NSA[2] | No change | No change | No data | No data |
| 6 | 4 | TRIS 5 mM | NaCl 137 mM | 7.0 | Purity (RP-HPLC) | 100% | 98.9% | 96.7% | 94.1% | 91.2% |
| | | | | | Covalent oligomers (SEC) | 0.07% | 0.12% | 0.14% | No data | 0.17% |
| | | | | | Visual inspection | Clear | Clear | Clear | Clear | Clear |
| | | | | | Physical stability[1] | NSA[2] | No change | No change | No change | No change |
| 7 | 4 | Phosphate 5 mM | NaCl 125 mM | 6.9 | Purity (RP-HPLC) | 100% | 98.7% | 97.4% | 94.0% | 91.0% |
| | | | | | Covalent oligomers (SEC) | 0.07% | 0.12% | 0.14% | No data | 0.17% |
| | | | | | Visual inspection | Clear | Clear | Clear | Clear | Clear |
| | | | | | Physical stability[1] | NSA[2] | No change | No change | No change | No change |
| 8 | 4 | Phosphate 2 mM | NaCl 125 mM | 7.0 | Purity (RP-HPLC) | 100% | 98.2% | 96.6% | 93.3% | 89.6% |
| | | | | | Covalent oligomers (SEC) | 0.07% | 0.12% | 0.15% | No data | 0.30% |

TABLE 4-continued

| # | CPD 1 (mg/ml) | Buffer | Tonicity agent | pH | Parameter | t = 0 | 1 M | 2 M | 3 M | 6 M |
|---|---|---|---|---|---|---|---|---|---|---|
| | | | | | Visual inspection | Clear | Clear | Clear | Clear | Clear |
| | | | | | Physical stability[1] | NSA[2] | No change | No change | No change | No change |

[1]ThT-one point, UV absorbance at 325 nM, or DLS;
[2]No signs of aggregation;
M: Month As exemplified by formulations 1-4, purity is higher for 5 mM concentrations of histidine and phosphate buffer than 20 mM concentrations. No or limited effect observed for visual appearance, physical stability, and covalent oligomers for histidine and phosphate buffer concentrations of 5 mM vs, 20 mM.

As exemplified by formulations 7-8, the beneficial effects of lowering buffer concentration to 5 mM phosphate are maintained at 2 mM phosphate.

Example 4: Accelerated Physical Stability in pH Range 6.1-6.9

CPD 1 drug product formulations #1-3 from Table 1 (Example 1) were filled into 1 ml Type 1 glass vials and subjected to physical stress in the form of steady rotation at approximately 15 rpm (rotations per minute) on a multi-rotator placed in a standard laboratory with window daylight (no light protection) and at room temperature, for the time periods indicated. Stability was determined as shown in the table.

TABLE 6

| # | CPD 1 (mg/ml) | Buffer | Tonicity agent | pH | Parameter | t = 0 | 1 w | 2 w | 3 w | 4 w |
|---|---|---|---|---|---|---|---|---|---|---|
| 1 | 4 | Phosphate 5 mM | Mannitol 230 mM | 6.1 | Covalent oligomers (SEC) | 0.07% | 0.14% | 0.15% | 0.15% | 0.16% |
| | | | | | Peptide particle size (DLS) | 3.2 nm | 4.3 nm | 3.2 nm | 3.3 nm | 4.8 nm |
| | | | | | Visual inspection | Clear | Clear | Clear | Clear | Clear |
| | | | | | Fibrillation (ThT) | No data | 2576 RFU | 2389 RFU | 2475 RFU | 3052 RFU |
| 2 | 4 | Phosphate 5 mM | Mannitol 230 mM | 6.5 | Covalent oligomers (SEC) | 0.08% | 0.15% | 0.14% | 0.15% | 0.15% |
| | | | | | Peptide particle size (DLS) | 2.8 nm | 4.0 nm | 5.1 nm | 4.0 nm | 3.4 nm |
| | | | | | Visual inspection | Clear | Clear | Clear | Clear | Clear |
| | | | | | Fibrillation (ThT) | No data | 2857 RFU | 2563 RFU | 2675 RFU | 3287 RFU |
| 3 | 4 | TRIS 20 mM | NaCl 118 mM | 6.9 | Covalent oligomers (SEC) | 0.08% | 0.13% | 0.14% | 0.14% | 0.14% |
| | | | | | Peptide particle size (DLS) | 3.1 nm | 3.6 nm | 3.5 nm | 3.5 nm | 3.2 nm |
| | | | | | Visual inspection | Clear | Clear | Clear | Clear | Clear |
| | | | | | Fibrillation (ThT) | No data | 1629 RFU | 1558 RFU | 1572 RFUU | 2088 RFU |

RFU: Relative fluorescent units;
w: week.

-

Formulations within the pH interval 6.1 to 6.9 are physically stable during 4 weeks rotation at room temperature.

Example 5: Chemical Stability or Solubility of Formulations with CPD 1 Concentrations from 0.4 mg/mL to 50 mg/mL A 4 mg/ml formulation of CPD 1 containing 20 mM TRIS and 118 mM NaCl was prepared as described in METHOD 1. The formulation was diluted with placebo buffer to reach a concentration of 0.4 mg/ml and analyzed after 24 hours storage at 25° C.

TABLE 7

| # | CPD 1 (mg/ml) | Buffer | Tonicity agent | pH | Parameter | t = 0 | 24 h |
|---|---|---|---|---|---|---|---|
| 4 | 0.4 | TRIS 20 mM | NaCl 118 mM | 6.6 | Purity (RP-HPLC) | 100% | 99.9% |

There was no decrease in purity after storage at the low concentration of 0.4 mg/ml, see Table 7.

To test solubility, CPD 1 was dissolved in alkaline MQW (pH adjusted with NaOH) by stirring.

TABLE 8

| # | CPD 1 (mg/ml) | Solvent | Solvent | Visual control |
|---|---|---|---|---|
| 5 | 50 | MQW | NaOH | Clear solution |
| 6 | 30 | MQW | NaOH | Clear solution |
| 7 | 25 | MQW | NaOH | Clear solution |
| 8 | 10 | MQW | NaOH | Clear solution |

CPD 1 could be dissolved to a clear solution in concentrations up to 50 mg/ml in MQW, see Table 8.

Example 6: Accelerated Chemical Stability at 40° C. Of Formulations with Buffer Concentrations of 0.5 to 40 mM at pH 6

Formulations in Tables A1-A3 were prepared according to METHOD I and filled into 1.5 ml LowBind Eppendorf tubes. No tonicity agent was included.

After 4 weeks storage at 40° C., stability was tested according to ASSAY II with the modification that results for covalent oligomer (SEC) formation (ASSAY IIb) are reported as the difference in total oligomers between the initial value and the 4 week time-point.

TABLE 9

| Purity (RP-HPLC) | | | | | | | |
|---|---|---|---|---|---|---|---|
| | | | | Buffer | | | |
| # | CPD1 (mg/ml) | Buffer conc. | pH | Phosphate | TRIS | Citrate | Histidine |
| 1-4 | 1 | 50 mM | 7 | 79.0% | ND | ND | ND |
| 5-8 | 1 | 40 mM | 7 | 82.2% | ND | ND | ND |
| 9-12 | 1 | 40 mM | 6 | 94.6%[1] | ND | ND | ND |
| 13-16 | 1 | 25 mM | 6 | 95.3% | 95.3% | 95.0% | ND |
| 17-20 | 1 | 20 mM | 6 | 95.9% | 95.6% | 96.1% | ND |
| 21-24 | 1 | 15 mM | 6 | 95.9% | 96.2% | 96.2% | ND |
| 25-28 | 1 | 10 mM | 6 | 95.6% | 96.0% | 96.4% | ND |
| 29-32 | 1 | 5 mM | 6 | 96.4% | 96.7% | 96.6% | 96.3% |
| 33-36 | 1 | 2 mM | 6 | 97.0% | 96.6% | ND | ND |
| 37-40 | 1 | 0.5 mM | 6 | 96.3% | 97.1% | 97.3% | ND |

[1]Average of results from 2 individual experiments;
ND: No data

TABLE 10

| Covalent oligomers (SEC) | | | | | | | |
|---|---|---|---|---|---|---|---|
| | | | | Buffer | | | |
| # | CPD1 (mg/ml) | Buffer conc. | pH | Phosphate | TRIS | Citrate | Histidine |
| 1-4 | 1 | 50 mM | 7 | 0.04% | ND | ND | ND |
| 5-8 | 1 | 40 mM | 7 | 0.03% | ND | ND | ND |
| 9-12 | 1 | 40 mM | 6 | 0.11%[1] | ND | ND | ND |
| 13-16 | 1 | 25 mM | 6 | 0.11% | 0.12% | 0.08% | ND |
| 17-20 | 1 | 20 mM | 6 | 0.13% | 0.15% | 0.08% | ND |
| 21-24 | 1 | 15 mM | 6 | 0.10% | 0.12% | 0.08% | ND |
| 25-28 | 1 | 10 mM | 6 | 0.11% | 0.13% | 0.10% | ND |
| 29-32 | 1 | 5 mM | 6 | 0.11% | 0.14% | 0.10% | 0.18% |
| 33-36 | 1 | 2 mM | 6 | 0.16% | 0.11% | ND | ND |
| 37-40 | 1 | 0.5 mM | 6 | 0.14% | 0.13% | 0.12% | ND |

[1]Average of results from 2 individual experiments;
ND: No data

TABLE 11

| # | CPD1 (mg/ml) | Buffer conc. (Total) | pH | Parameter | Buffer Phosphate/ TRIS 1:1 | Phosphate/ Citrate 1:1 | Phosphate/ Histidine 1:1 |
|---|---|---|---|---|---|---|---|
| 1-3 | 1 | 5 mM | 6 | Purity (RP-HPLC) | 96.6% | 96.3% | 95.9% |
| | | | | Covalent oligomers (SEC) | 0.14% | 0.16% | 0.18% |

At pH 6, decrease in purity is reduced when buffer concentration is lowered (Table 9). Buffer concentration has no significant effect on formation of covalent oligomers (Table 10).

Total buffer concentration appears to be the most significant factor. Switching from a single buffer at 5 mM to a mixture of two buffers each at 2.5 mM appears to have no significant effect. (Compare Table 11 with Table 9 and 10, formulations 29-32.)

Example 7: Accelerated Chemical and Physical Stability at 25° C. Of Formulations with Varying Concentrations of Compound 1

Formulations in Table 12 were prepared according to METHOD I and filled into siliconised 1 ml Type 1 glass cartridges fitted with bromobutyl plungers. Stability was tested according to ASSAY II and ASSAYs IIIa, IIIb and IIIc, after storage at 2500 for the time period indicated.

TABLE 12

| # | CPD 1 (mg/ml) | Buffer | Tonicity agent | pH | Parameter | 0 M | 1 M | 3 M | 6 M |
|---|---|---|---|---|---|---|---|---|---|
| 1 | 10 | Phosphate 5 mM | Mannitol 260 mM | 6.5 | Purity (RP-HPLC) | 100.0% | 99.1% | 98.1% | 96.3% |
| | | | | | Covalent oligomers (SEC) | 0.03% | 0.13% | 0.15% | 0.18% |
| | | | | | Visual inspection | Clear | Clear | Clear | Clear |
| | | | | | Physical stability[1] | NSA[2] | No change | No change | No change |
| 2 | 5 | Phosphate 5 mM | Mannitol 260 mM | 6.5 | Purity (RP-HPLC) | 100.0% | 99.1% | 98.1% | 96.3% |
| | | | | | Covalent oligomers (SEC) | 0.02% | 0.12% | 0.14% | 0.17% |
| | | | | | Visual inspection | Clear | Clear | Clear | Clear |
| | | | | | Physical stability[1] | NSA[2] | No change | No change | No change |
| 3 | 1 | Phosphate 5 mM | Mannitol 260 mM | 6.5 | Purity (RP-HPLC) | 100.0% | 99.4% | 98.3% | 96.4% |
| | | | | | Covalent oligomers (SEC) | 0.07% | 0.11% | 0.13% | 0.16% |
| | | | | | Visual inspection | Clear | Clear | Clear | Clear |
| | | | | | Physical stability[1] | NSA[2] | No change | No change | No change |
| 4 | 5 | Citrate 5 mM | Mannitol 260 mM | 6.5 | Purity (RP-HPLC) | 100.0% | 99.2% | 98.5% | 96.6% |
| | | | | | Covalent oligomers (SEC) | 0.03% | 0.13% | 0.14% | 0.18% |
| | | | | | Visual inspection | Clear | Clear | Clear | Clear |
| | | | | | Physical stability[1] | NSA[2] | No change | No change | No change |

[1]ThT-one point, UV absorbance at 325 nm, and DLS;
[2]No signs of aggregation;
M: Month Varying CPD 1 concentration in the tested range of 1-10 mg/ml had no effect on chemical and physical stability.

Example 8: Accelerated Chemical Stability at 25° C. Of Formulations Containing Different Tonicity Agents Formulations in Table 13 were prepared according to METHOD I and filled into 1 ml Type 1 glass vials. Stability was tested according to ASSAY II after storage at 25° C. for the time period indicated.

TABLE 13

| # | CPD 1 (mg/ml) | Buffer | Tonicity agent | pH | Parameter | 0 M | 1 M | 3 M | 6 M |
|---|---|---|---|---|---|---|---|---|---|
| 1 | 4 | Phosphate 5 mM | Mannitol 260 mM | 6.6 | Purity (RP-HPLC) | 100.0% | 99.7% | 97.9% | 96.1% |
| | | | | | Covalent oligomers (SEC) | 0.08% | 0.14% | 0.16% | 0.17% |
| 2 | 4 | Phosphate 5 mM | Propylene glycol 230 mM | 6.6 | Purity (RP-HPLC) | 100.0% | 98.9% | 97.3% | 95.7% |
| | | | | | Covalent oligomers (SEC) | 0.09% | 0.12% | 0.14% | 0.16% |
| 3 | 4 | Phosphate 5 mM | NaCl 118 mM | 6.6 | Purity (RP-HPLC) | 100.0% | 98.9% | 96.6% | 93.6% |
| | | | | | Covalent oligomers (SEC) | 0.11% | 0.11% | 0.13% | 0.15% |
| 4 | 4 | Phosphate 5 mM | Glycerol 5 mM | 6.5 | Purity (RP-HPLC) | 100.0% | ND | 92.3% | 89.0% |
| | | | | | Covalent oligomers (SEC) | 0.09% | 0.24% | 1.3% | 2.4% |

M: Month;
ND: No data

Decrease in purity appears to be lower for formulations with mannitol and propylene glycol as tonicity agent than for formulations with glycerol and NaCl as tonicity agent. Formation of covalent oligomers appears to be higher with glycerol as a tonicity agent than with other tonicity agents.

The following paragraphs (paras.) set out certain embodiments of the invention.

1. A stable aqueous liquid pharmaceutical formulation comprising an amylin analogue, which is:

[19CD]-isoGlu-RD( )GTATK( )ATERLA-Aad-FLQRSSF-Gly(Me)-A-Ile(Me)-LSSTEVGSNT-Hyp-$NH_2$ (SEQ ID NO: 3)

or a pharmaceutically acceptable salt and/or derivative thereof;

wherein the formulation comprises:

(a) the amylin analogue at a concentration of from about 0.4 mg/ml to about 25 mg/ml; and (b) a buffer at a concentration of about 0.5 mM to about 25 mM;

wherein the formulation has a pH of about 5.8 to about 6.9.

2. The stable aqueous liquid formulation of para. 1, wherein the amylin analogue is present at a concentration of at least about 0.4 mg/ml, at least about 0.5 mg/ml, at least about 0.6 mg/ml, at least about 1.2 mg/ml, or at least about 2.5 mg/ml.

3. The stable aqueous liquid formulation of any one of the preceding paras., wherein the amylin analogue is present at up to about 25 mg/ml, up to about 20 mg/ml, up to about 15 mg/ml, or up to about 10 mg/ml.

4. The stable aqueous liquid formulation of any one of the preceding paras., wherein the amylin analogue is present at a concentration of about 3 mg/ml to about 12 mg/ml, e.g. about 3 mg/ml to about 7 mg/ml or about 8 mg/ml to about 12 mg/ml, e.g. about 5 mg/ml or about 10 mg/ml.

5. The stable aqueous liquid formulation of any one of the preceding paras., wherein the buffer is present at a concentration of about 0.5 mM to about 20 mM, e.g. about 0.5 mM to about 15 mM, e.g. about 1 mM to about 15 mM, e.g. about 1 mM to about 12 mM.

6. The stable aqueous liquid formulation of any one of the preceding paras., wherein the buffer is present at a concentration of about 3 mM to about 7 mM or about 8 mM to about 12 mM, e.g. about 5 mM or about 10 mM.

7. The stable aqueous liquid formulation of any one of the preceding paras., wherein the buffer is phosphate, histidine or citrate.

8. The stable aqueous liquid formulation of any one of paras. 1 to 6, wherein the buffer is TRIS buffer, and wherein the buffer is present at about 15 mM to about 25 mM, e.g. about 17 mM to about 23 mM, e.g. about 20 mM 9. The stable aqueous liquid formulation of any one of the preceding paras., wherein the pH is about 6.2 to about 6.8, e.g. about 6.4 to about 6.6, e.g. about 6.5.

10. The stable aqueous liquid formulation of any one of the preceding paras., further comprising a tonicity modifier.

11. The stable aqueous liquid formulation of any one of the preceding paras., wherein the formulation is stable at 2-8° C. for at least 6 months, at least 12 months, at least 18 months or at least 24 months.

12. The stable aqueous liquid formulation of any one of the preceding paras., wherein the formulation displays substantially no turbidity, or aggregation, fibrillation or gelling of the amylin analogue, after storage at 2-8° C. for at least 6 months, at least 12 months, at least 18 months or at least 24 months.

13. The stable aqueous liquid formulation of any one of the preceding paras., wherein at least 80%, more preferably at least 85%, at least 90%, at least 95%, at least 96%, at least 97%, at least 98%, or at least 99% of the amylin analogue remains in intact monomeric form in the formulation after it has been stored at 2-8° C. for at least 6 months, at least 12 months, at least 18 months or at least 24 months.

14. The stable aqueous liquid formulation of any one of the preceding paras., wherein the amylin analogue is provided as a chloride salt.

15. The stable aqueous liquid formulation of any one of the preceding paras., wherein the water is the sole solvent used to make the aqueous liquid formulation.

16. The stable aqueous liquid formulation of any one of the preceding paras., wherein the formulation is formulated for administration to a subject by injection.

17. The stable aqueous liquid formulation of para. 16, wherein the injection is subcutaneous injection.

18. The stable aqueous liquid formulation of any one of the preceding paras., wherein the formulation is sterile.

19. A container or delivery device comprising the liquid formulation of any one of the preceding paras.

20. The stable aqueous liquid formulation of any one of paras. 1 to 18, for use in a method of medical treatment.

21. The stable aqueous liquid formulation of any one of paras. 1 to 18 for use in a method of treating, inhibiting or reducing weight gain, promoting weight loss and/or reducing excess body weight.

22. The stable aqueous liquid formulation of any one of paras. 1 to 18 for use in a method of treating obesity (e.g. morbid obesity, obesity prior to surgery), obesity-linked inflammation, obesity-linked gallbladder disease, obesity-induced sleep apnea, degeneration of cartilage, osteoarthritis, or reproductive health complications of obesity or overweight.

23. The stable aqueous liquid formulation of any one of paras. 1 to 18 for use in a method of prevention or treatment of Alzheimer's disease, diabetes (e.g. type 1 diabetes, type 2 diabetes), pre-diabetes, insulin resistance syndrome, impaired glucose tolerance (IGT), metabolic syndrome, hyperglycemia, hypertension, atherogenic dyslipidemia, hepatic steatosis ("fatty liver"; e.g. non-alcoholic fatty liver disease (NAFLD), non-alcoholic steatohepatitis (NASH)), kidney failure, arteriosclerosis (e.g. atherosclerosis), macrovascular disease, microvascular disease, diabetic heart disease (e.g. diabetic cardiomyopathy), coronary heart disease, peripheral artery disease or stroke.

24. The stable aqueous liquid formulation of any one of paras. 1 to 18 for use in a method of lowering circulating LDL levels and/or increasing HDL/LDL ratio.

25. A process for producing a stable aqueous pharmaceutical formulation comprising an amylin analogue, which is:

```
                                        (SEQ ID NO: 3)
[19CD]-isoGlu-RD( )GTATK( )ATERLA-Aad-FLQRSSF-

Gly(Me)-A-Ile(Me)-LSSTEVGSNT-Hyp-NH2
```

or a pharmaceutically acceptable salt and/or derivative thereof; the process comprising formulating (a) the amylin analogue at a concentration of from about 0.4 mg/ml to about 25 mg/ml; and (b) a buffer at a concentration of about 0.5 mM to about 25 mM;

to produce the stable aqueous liquid formulation, wherein the formulation has a pH of about 5.8 to about 6.9.

26. A formulation produced by the process of para. 25, wherein the formulation is a stable aqueous liquid formulation of any one of paras. 1 to 18.

The invention claimed is:

1. A stable aqueous liquid pharmaceutical formulation comprising an amylin analogue, which is:

(SEQ ID NO: 3)

[19CD]-isoGlu-RD( )GTATK( )ATERLA-Aad-FLQRSSF-Gly(Me)-A-Ile(Me)-LSSTEVGSNT-Hyp-$NH_2$ wherein "[19CD]" represents 19-carboxy-nonadecanoyl-; and "( )" shown after the amino acid residues indicate residues whose side chains participate in an intramolecular lactam bridge;

or a pharmaceutically acceptable salt thereof;

wherein the formulation comprises:

(a) the amylin analogue at a concentration of from about 0.4 mg/ml to about 25 mg/ml; and (b) a buffer at a concentration of about 0.5 mM to about 25 mM;

wherein the formulation has a pH of about 6.2 to about 6.8, and wherein the formulation is formulated for administration to a subject by injection.

2. The stable aqueous liquid formulation of claim 1, wherein the amylin analogue is present at a concentration of at least about 1.2 mg/ml.

3. The stable aqueous liquid formulation of claim 1, wherein the amylin analogue is present at up to about 20 mg/ml.

4. The stable aqueous liquid formulation of claim 1, wherein the amylin analogue is present at a concentration of about 3 mg/ml to about 12 mg/ml.

5. The stable aqueous liquid formulation of claim 1, wherein the buffer is present at a concentration of about 0.5 mM to about 20 mM.

6. The stable aqueous liquid formulation of claim 5, wherein the buffer is present at a concentration of about 3 mM to about 7 mM.

7. The stable aqueous liquid formulation of claim 1, wherein the buffer is phosphate, histidine or citrate.

8. The stable aqueous liquid formulation of claim 1, wherein the buffer is TRIS buffer, and wherein the buffer is present at about 15 mM to about 25 mM.

9. The stable aqueous liquid formulation of claim 1, wherein the pH is about 6.5.

10. The stable aqueous liquid formulation of claim 1, further comprising a tonicity modifier.

11. The stable aqueous liquid formulation of claim 1, wherein the formulation is stable at 2-8° C. for at least 6 months.

12. The stable aqueous liquid formulation of claim 1, wherein the formulation displays substantially no turbidity, or aggregation, fibrillation or gelling of the amylin analogue, after storage at 2-8° C. for at least 6 months.

13. The stable aqueous liquid formulation of claim 1, wherein at least 80% of the amylin analogue remains in intact monomeric form in the formulation after it has been stored at 2-8° C. for at least 6 months.

14. The stable aqueous liquid formulation of claim 1, wherein the amylin analogue is provided as a chloride salt.

15. The stable aqueous liquid formulation of claim 1, wherein the amylin analogue is present at a concentration of about 1.2 mg/ml to about 18 mg/ml.

16. The stable aqueous liquid formulation of claim 1, wherein the amylin analogue is present at a concentration of about 1.2 mg/ml to about 10 mg/ml.

17. The stable aqueous liquid formulation of claim 15, wherein the amylin analogue is present at a concentration of about 2 mg/ml.

18. The stable aqueous liquid formulation of claim 4, wherein the amylin analogue is present at a concentration of about 12 mg/ml.

19. The stable aqueous liquid formulation of claim 1, wherein the amylin analogue is present at a concentration of about 18 mg/ml.

* * * * *